United States Patent
Lee et al.

(10) Patent No.: US 6,353,152 B1
(45) Date of Patent: Mar. 5, 2002

(54) CORTICOTROPIN RELEASING FACTOR RECEPTOR 2 DEFICIENT MICE AND USES THEREOF

(75) Inventors: Kuo-Fen Lee, Del Mar; Wylie W. Vale, La Jolla; Tracy L. Bale, San Diego, all of CA (US); George W. Smith, Mason, MI (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/616,937

(22) Filed: Jul. 14, 2000

Related U.S. Application Data

(60) Provisional application No. 60/144,261, filed on Jul. 15, 1999, now abandoned.

(51) Int. Cl.$^7$ ...................... A01K 67/027; A01K 67/00; G01N 33/00
(52) U.S. Cl. .................. 800/18; 800/3; 800/9
(58) Field of Search .............................. 800/18, 21, 22, 800/25, 3; 435/455, 463, 320.1, 325

(56) References Cited

PUBLICATIONS

Moreadith et al.; Gene targeting in embryonic stem cells: the new physiology and metabolism, 1997, J Moi. Med. 75:208–216.*

Capecchi et. al.; Targeted Gene Replacement, 1994, Scientific American:34–41.*

Perrin et al.; Identification of a second corticotropin–releasing factor receptor gene and characterization of a cDNA expressed in heart, 1995, Proc. Natl. Acad. Sci. vol. 92:2969–2973.*

* cited by examiner

*Primary Examiner*—Deborah Crouch
*Assistant Examiner*—Thaian N. Ton
(74) *Attorney, Agent, or Firm*—Benjamin Aaron Adler

(57) ABSTRACT

The present invention provides transgenic mice deficient in corticotropin releasing factor receptor 2. Corticotropin releasing factor is a critical integrator of the hypothalamic-pituitary-adrenal axis in response to stress. CRF and its related molecule urocortin bind CRF receptor 1 and CRFR2 with distinct affinities. CRFR2 mutant mice were hypersensitive to stress and displayed increased anxiety-like behavior. Mutant mice had normal basal feeding and weight gain, but exhibited decreased food intake following food deprivation. Intravenous UCN dramatically decreased the mean arterial pressure in the controls but had no effect in the mutants. A deficiency of CRFR2 results in a significant increase in urocortin mRNA in the rostral region of the Edinger Westphal and a significant increase in CRF mRNA in central nucleus of the amygdala. These results demonstrate that the CRFR2 mutant mice, opposed to CRFR1 mutant mice, have an increased sensitivity to stress and display anxiety-like behavior. These mice are useful for the study of anxiety, depression, and the physiology of the HPA axis.

11 Claims, 22 Drawing Sheets

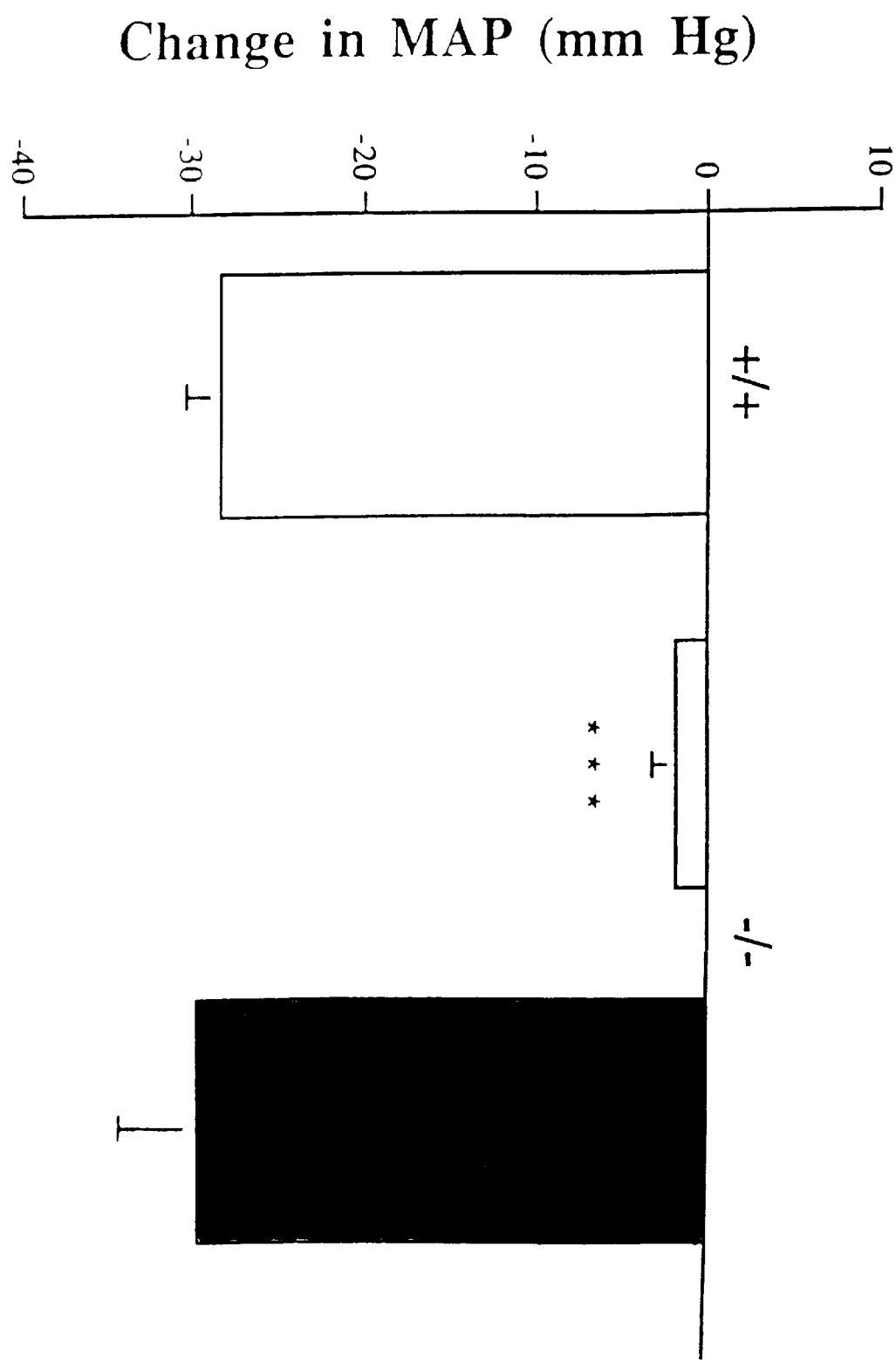

CORTICOTROPIN RELEASING FACTOR RECEPTOR 2 DEFICIENT MICE AND USES THEREOF

This non-provisional application claims benefit of priority of provisional applications U.S. Ser. No. 60/144,261 filed Jul. 15, 1999, now abandoned.

FEDERAL FUNDING LEGEND

This invention was produced in part using funds from the Federal government under grant no. NIH DK-26741 and NRSA fellowships DK09841 and DK09551. Accordingly, the Federal government has certain rights in this invention.

BACKGROUND OF THE INVENTION

1. Field of the Invention

The present invention relates generally to the fields of neurobiology, endocrinology, and psychiatry. More specifically, the present invention relates to the study of anxiety and to mice deficient for corticotropin releasing factor receptor 2.

2. Description of the Related Art

Corticotropin releasing factor (CRF) is a critical coordinator of the hypothalamic-pituitary-adrenal (HPA) axis. In response to stress, corticotropin releasing factor released from the paraventricular nucleus of the hypothalamus (PVN) activates corticotropin releasing factor receptors on anterior pituitary corticotropes, resulting in release of adrenocorticotropic hormone (ACTH) into the bloodstream. ACTH in turn activates ACTH receptors in the adrenal cortex to increase synthesis and release of glucocorticoids (1).

The receptors for CRF, CRFR1 and CRFR2 are localized throughout the CNS and periphery. While CRF has a higher affinity for CRFR1 than for CRFR2, urocortin (UCN), a CRF-related peptide, is thought to be the endogenous ligand for CRFR2 since it binds with almost 40-fold higher affinity than does CRF (2). CRFR1 and CRFR2 share approximately 71% amino acid sequence similarity and are distinct in their localization within the brain and peripheral tissues (3–6). CRFR1 is expressed mainly in the pituitary gland, cortex, cerebellum, hindbrain, and olfactory bulb, whereas CRFR2 is found in the lateral septum, ventral medial hypothalamus (VMH), choroid plexus, and many peripheral sites (5, 7, 8). CRFR2 has several isoforms, one of which has been shown to not bind any known ligand (9).

Mice deficient for CRFR1 have decreased HPA axis hormone levels, an impaired stress response, and decreased anxiety-like behavior (10, 11). These results coincide with those obtained using CRFR1 specific antagonists in vivo (12–14). In contrast, CRFR2 specific antagonists are not currently available, and since its cloning in 1995, little has been elucidated regarding the physiological function of CRFR2. UCN may be the endogenous ligand for CRFR2 and has been shown to be a modulator of feeding when administered centrally (15). Since CRFR2 is localized to the ventral medial hypothalamus, a central site of food intake regulation and satiety, it is possible that urocortin actions on these receptors may affect feeding. Further, peripheral administration of urocortin results in hypotension (2, 16) which may result from the action of CRFR2 in the vasculature (5, 8).

The prior art is deficient in the lack of mice deficient for corticotropin releasing factor receptor 2. The present invention fulfills this longstanding need and desire in the art.

SUMMARY OF THE INVENTION

In order to discern the developmental and physiological roles of CRFR2, CRFR2 null mutant mice were generated and analyzed. CRFR2 deficient mice exhibit increased anxiety-like behavior and a hypersensitive HPA axis in response to stress. CRFR1 and CRFR2 mutant mice provide valuable models of anxiety and depression and may further help delineate the molecular mechanisms underlying these diseases. Study of the corticotropin releasing factor signaling pathway and its role in the management of anxiety and depression may provide the necessary clues required for the effective treatment of these diseases.

Thus, the present invention is directed to a non-natural transgenic mouse with a disruption in at least one allele of the corticotropin releasing factor receptor 2 (CRFR2) such that said mouse does not express corticotropin releasing factor receptor 2 protein from said allele. Preferably, the DNA sequences for exons 10, 11, and 12 of said corticotropin releasing factor receptor 2 allele have been deleted. The transgenic mouse may have these DNA sequences replaced with a neomycin resistance gene cassette. The transgenic mouse may be either heterozygous or homozygous for this replacement. Also included in an embodiment of the present invention are the progeny of a mating between a mouse of the present invention and a mouse of another strain.

Another embodiment of the present invention is the application of a CRFR2 deficient mouse to the study anxiety or depression and to test the effects of a compound on anxiety or depression. For example, a method is provided of screening a compound for anxiety modulating activity, comprising the steps of: a) administering said compound to the transgenic mouse of the present invention; b) testing said mouse for anxiety-related behavior; and c) comparing anxiety-like behavior of said mouse with anxiety-like behavior in a second transgenic mouse of the present invention to which said compound was not administered. In addition, a method of screening a compound for depression-modulating activity is provided, comprising the steps of: a) administering said compound to the transgenic mouse of the present invention; b) testing said mouse for depression-like behavior; and c) comparing depression-like behavior of said mouse with depression-like behavior in a second transgenic mouse of the present invention to which said compound was not administered.

Yet another embodiment of the present involves the use of a CRFR2 deficient mouse in a similar procedure to screen for compounds which affect blood pressure or angiogenesis.

A further embodiment of the current invention is the application of the CRFR2 deficient mice to the study of the physiology of the HPA axis, e.g., a method of screening a compound for effects on the response of the hypothalamic-pituitary-adrenal axis to stress, comprising the steps of: a) administering said compound to a transgenic mouse of the present invention; b) placing said mouse in a stress-inducing situation; c) monitoring plasma levels of corticosterone and adrenocorticotropic hormone in said mouse; and d) comparing said levels to those in a transgenic mouse of the present invention not placed in said stress-inducing situation.

In yet another embodiment of the current invention, the mice can be used to study the effects of a compound on the response of the HPA axis to stress by monitoring plasma levels of corticosterone and ACTH.

Yet another embodiment of the current invention relates to the use of the mice of the instant invention in the study the effect of corticotropin releasing factor receptor 2 on other proteins such as corticotropin releasing factor and urocortin.

A further embodiment of the current invention is the use of the CRFR2 deficient mice to examine CRFR1 responses unhindered by the presence of CRFR2.

Yet another embodiment of the instant invention is the manipulation of CRFR2 activity to stimulate or inhibit vascularization.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A is a representation of the genomic organization of the CRFR2 gene showing the deletion of exons 10, 11, and 12 which code for half of transmembrane domain five through the end of transmembrane domain seven. The targeting construct utilized for homologous recombination is also shown.

In FIG. 1B, the disrupted allele was detected by Southern Blot analysis of tail DNA isolated from wild type (+/+), heterozygote (+/−), and null mutant (−/−) mice.

FIG. 1C presents the results of autoradiographic binding of $^{125}$I-Sauvagine in CRFR2 control (top) and mutant (bottom) mice. Note, no CRFR2 binding in the lateral septum of CRFR2 mutant mice, while the CRFR1 cortical binding is similar to that of the control mouse.

FIG. 1D shows hematoxylin and eosin (H&E) staining of the adrenal glands. Note no difference in adrenal gland size (upper panels) at 10× magnification or structure (lower panels) at 20× magnification, C, cortex; M, medulla; ZG, zona glomerulosa; ZF, zona fasciculata; ZR, zona reticularis; n=8.

FIG. 1E shows H&E staining of the pituitary glands which were mounted on liver for tissue sectioning (upper panels) at 4× magnification, n=8. Pituitary corticotropes were identified with anti-ACTH antibodies (20) (lower panels) at 10× magnification, n=5. P, posterior lobe; I, intermediate lobe; A, anterior lobe. No gross anatomical differences were observed for the pituitary gland or for the corticotrope localization or expression levels of ACTH.

FIG. 2A shows pre-stress ACTH plasma levels at 7:00 AM, n=16.

FIG. 2B shows basal corticosterone plasma levels for 7:00 AM and 5:00 PM, n=7.

FIG. 2C presents a time course of restraint stress effects on ACTH.

FIG. 2D demonstrates that corticosterone plasma levels at 7:00 AM are significantly different in null mutant mice from wild type controls at same time point, n=7.

FIG. 3A shows food consumption of mutant mice (n=7) basal and following a 24 hr food deprivation period as compared to wild type litter mates (n=10), p<0.001 by Scheffe post-hoc test.

FIG. 3B shows the weight of wild type and mutant mice, both the basal (open bars) weights and following 24 hrs of refeeding (black bars) following the food deprivation period. Note that there are no differences between the groups in basal or refed body weights.

FIG. 4A shows that in male mice the percentage of time spent in the open arms (**, p<0.005) and number of visits to the open arms (*, p<0.02) were significantly less for the mutant mice than for the wild type controls (control n=7, mutant n=7; mean ±SEM).

FIG. 4B shows the same test as FIG. 4A for female mice. The percentage of time spent in the open arms (**, p<0.03) and number of visits to the open arms (*, p<0.03) were significantly less for the mutant mice than for the wild type controls (control n=9, mutant n=12; mean ±SEM).

FIGS. 4C and 4D show that locomotor activity was not different between control and mutant animals (FIG. 4C, male mice; FIG. 4D, female mice) as measured by total closed arm entries and total arm entries.

FIG. 4E shows that no differences were found in anxiety-like behavior measured in the light/dark box experiment for time spent in light portion of the box.

FIG. 4F shows that no differences were found in anxiety-like behavior measured in the light/dark box experiment for the number of transitions between the light and dark portions.

FIG. 4G shows the amount of time spent in the inner squares of the open field apparatus (*, p<0.05).

FIG. 4H shows the present of total crossings occurring in the inner squares (**, p<0.01; controls, n=5; mutants n=7; mean ±SEM).

FIG. 5A shows silver grains resulting from in situ hybridization for urocortin mRNA in the rostral EW (upper) at 20× magnification and CRF mRNA in cAmyg (middle) and paraventricular nucleus (lower) at 10× magnification.

FIG. 5B presents the semi-quantitative analysis of silver grains used to determine cell numbers expressing urocortin mRNA in the rostral EW.

FIG. 5C shows the average optical density of urocortin mRNA per cell.

FIG. 5D shows the optical density of CRF mRNA in the cAmyg.

FIG. 5E shows the optical density of CRF mRNA in the paraventricular nucleus.

FIG. 6 shows cardiovascular responses to intravenous infusion of 1.0 µg urocortin in wild type (n=5) and mutant mice (n=3) (black bars). Note the remarkable muted response of mutant mice to the urocortin injection. *** p<0.005. CRFR2 mutant mice also received a second infusion of sodium nitroprusside (0.8 µg in 100 µl of 0.9% saline) following recovery of arterial pressure from the UCN infusion (open bar). The mean arterial pressure (MAP) was determined from the blood pressure tracings.

DETAILED DESCRIPTION OF THE INVENTION

Figure 1A:
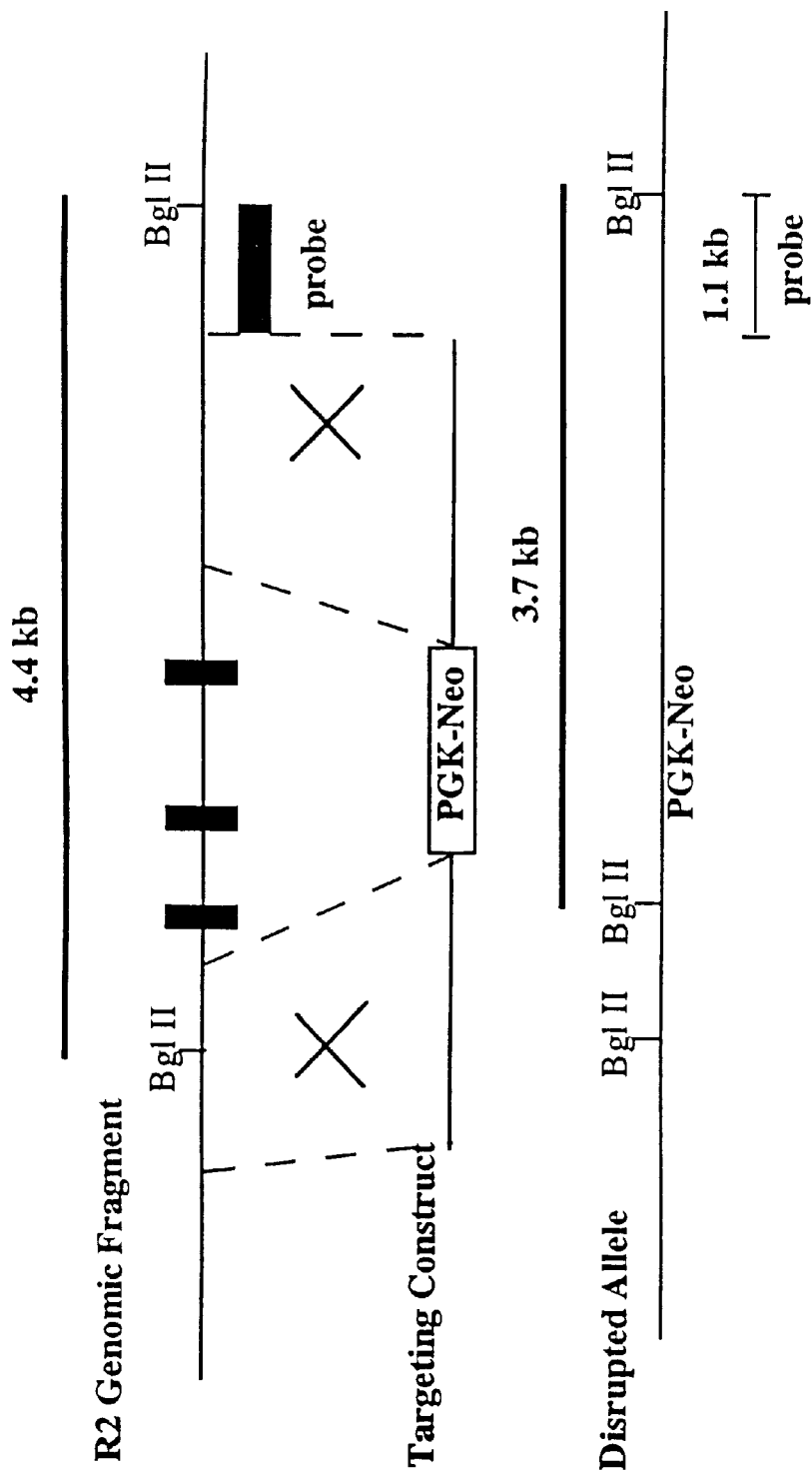
FIGS. 1A–1E show the procedure used for the generation of CRFR2-Deficient Mice, the detection of mutant mice, and the effects therein.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins Eds. (1985)]; "Transcription and Translation" [B. D. Hames & S. J. Higgins Eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of aminoterminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide N-terminal to the polypeptide that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nuclcotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to mice deficient for CRFR2, which were generated to discern the developmental and physiological roles of CRFR2 in anxiety and HPA axis circuitry. This was done by deleting exons 10, 11, and 12 of corticotropin releasing factor receptor 2. In the present invention, these sequences have been replaced with a neomycin resistance gene cassette. The mice may be either heterozygous of homozygous for the CRFR2 deficiency and may be crossed with mice of another strain.

The present invention is also directed to the application of the CRFR2 deficient mice in the study of anxiety and depression, including methods of testing a compound for anxiety or depression modulating activity. Compounds which affect blood pressure and angiogenesis can also be screened using the CRFR2 mice.

The current invention is also directed to use of the CRFR2 deficient mice in the study of the molecular physiology of the hypothalamic-pituitary-adrenal (HPA) axis. The mice can be used to test the effects of a compound on the response of the HPA axis to stress.

The current invention is also directed to the use of the transgenic mice to study the molecular functions of corticotropin releasing factor receptor 2 on corticotropin releasing factor, corticotropin releasing factor receptor 1, urocortin, and other CRF and urocortin receptors.

In addition, the present invention can be used to study the responses and activities of CRFR1 in a CRFR2 negative environment. In this manner, CRFR1 responses can be studied unhindered by CRFR2 modulation.

The instant invention is also directed the use of agonist or antagonist of CRFR2 activity to stimulate or inhibit vascularization. The use of agonist to stimulate CRFR2 activity may be useful for the inhibition of vascularization for the treatment of cancer.

The following examples are given for the purpose of illustrating various embodiments of the invention and are not meant to limit the present invention in any fashion.

EXAMPLE 1

Generation of the CRFR2 Deficient Mice

For the construction of CRFR2 null mutant mice, a genomic clone DNA containing the CRFR2 locus was isolated from a mouse strain 129 genomic DNA library. From this clone, a targeting vector was constructed in which the exons 10, 11, and 12 of the CRFR2 gene encoding the beginning of the fifth transmembrane domain through the end of the seventh transmembrane domain were replaced with a neomycin resistance gene cassette (FIG. 1A). The resulting plasmid DNA was linearized with Not I and electroporated into J1 embryonic stem (ES) cells as previously described (10). After selection in 0.2 mg/ml G418 (active form) for 7–9 days, neomycin resistant clones were individually selected and screened for the presence of the disrupted CRFR2 allele by Southern blot analysis.

Figure 1B:
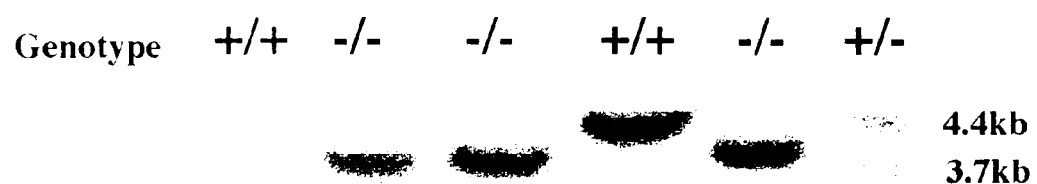

Positive ES clones were injected into C57BL/6 blastocysts to generate chimeric mice. Chimeric males were crossed to chimeric females producing C57BL/6-129 mixed background mice. Germ-line transmission of the disrupted allele was detected by Southern analysis of tail DNA collected from F1 pups displaying agouti coat color (FIG. 1B).

EXAMPLE 2

Analysis of CRFR1 and CRFR2 Expression in CRFR2 Deficient Mice

To determine if the targeted deletion resulted in a null mutation of the CRFR2 gene, receptor autoradiography was performed on brain sections from wild type control and mutant animals.

Slides containing 20 µm sectioned brain tissue were thawed at room temperature and washed twice for 10 min. in 50 mM Tris buffer (pH 7.4) at room temperature. Sections were then incubated in buffer containing 50 mM Tris (pH 7.4), $^{125}$I-Sauvagine, 10 mM $MgCl_2$, 0.1% BSA, and 0.05% bacitracin for 60 min. at room temperature. Sauvagine is a CRF-related peptide and an agonist at the CRF receptors. Nonspecific binding was defined in adjacent sections which were exposed to both $^{125}$I-Sauvagine and 1 μm cold sauvagine. After the incubation period, slides were washed in a 50 mM Tris buffer plus 0.01% Triton X-100 at 4° C. twice for 5 min. each. Slides were rapidly dipped in deionized water, dried and apposed to film for 3 days.

Figure 1C:
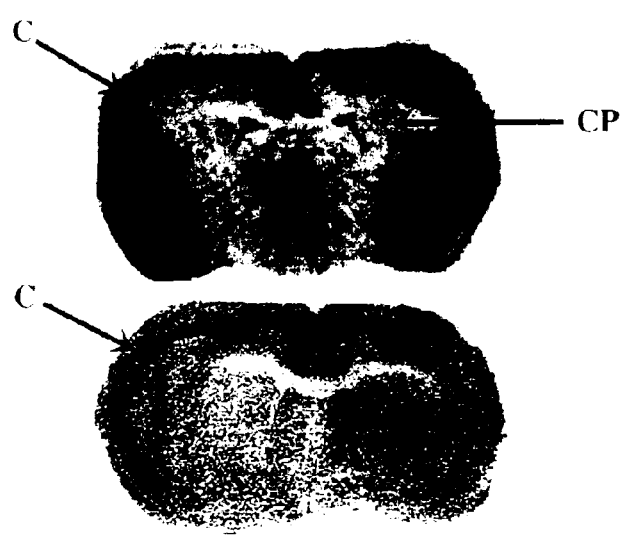

In the mutant mice, no binding in brain regions specific to CRFR2 (lateral septum) was detected, yet binding to CRFR1 in the cortex was retained (FIG. 1C). These results demonstrate that the disruption of the CRFR2 gene resulted in a null mutation in these mice. Mutant mice were fertile and transmitted the mutant allele in a Mendelian fashion.

EXAMPLE 3
Histological Analysis of CRFR2 Deficient Mice

Figure 1D:
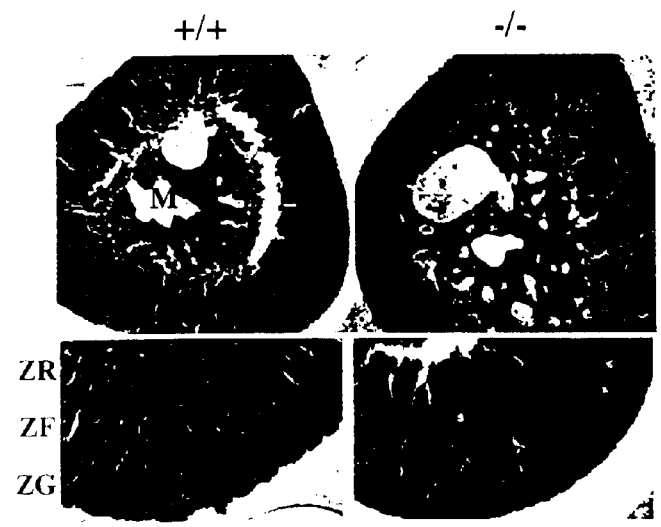
Figure 1E:
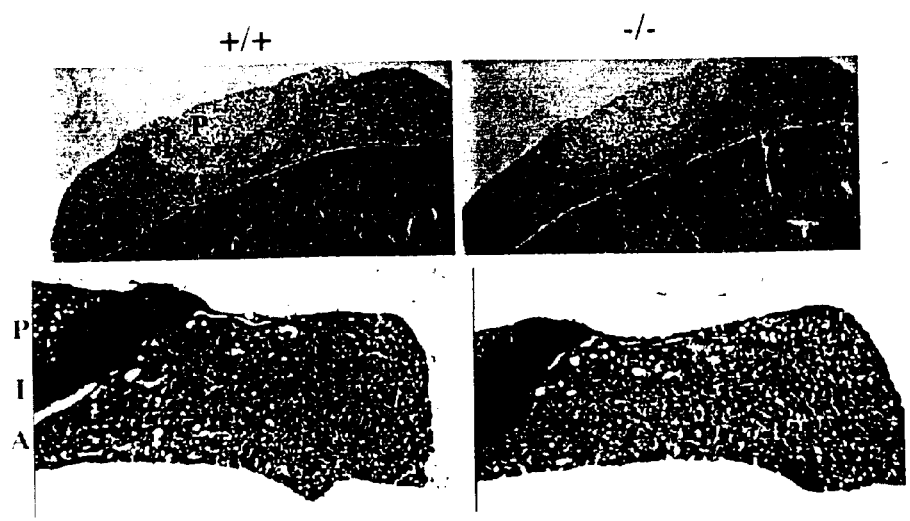

To determine whether the development of the HPA axis was compromised in the CRFR2 deficient mice, the pituitary and adrenal glands of male mice 10–12 week of age were sectioned and stained with hematoxylin and eosin (H&E). Briefly, mice were perfused with 4% paraformaldehyde (PFA). Tissues were removed, postfixed overnight at 4 C., and cryoprotected in 30% sucrose in PBS. Tissues were sectioned at 12 μm thickness and stained with hematoxylin and eosin. The results showed no obvious differences in structure or cell types (FIGS. 1D–1E).

In addition, pituitary sections were stained with anti-ACTH antibodies. The pituitaries were sectioned, postfixed in 4% PFA for 5 min., rinsed in PBS, and stained with ACTH antibody as described previously (10). No qualitative differences were noted between wild type and mutant corticotropes (FIG. 1E).

Figure 2A:
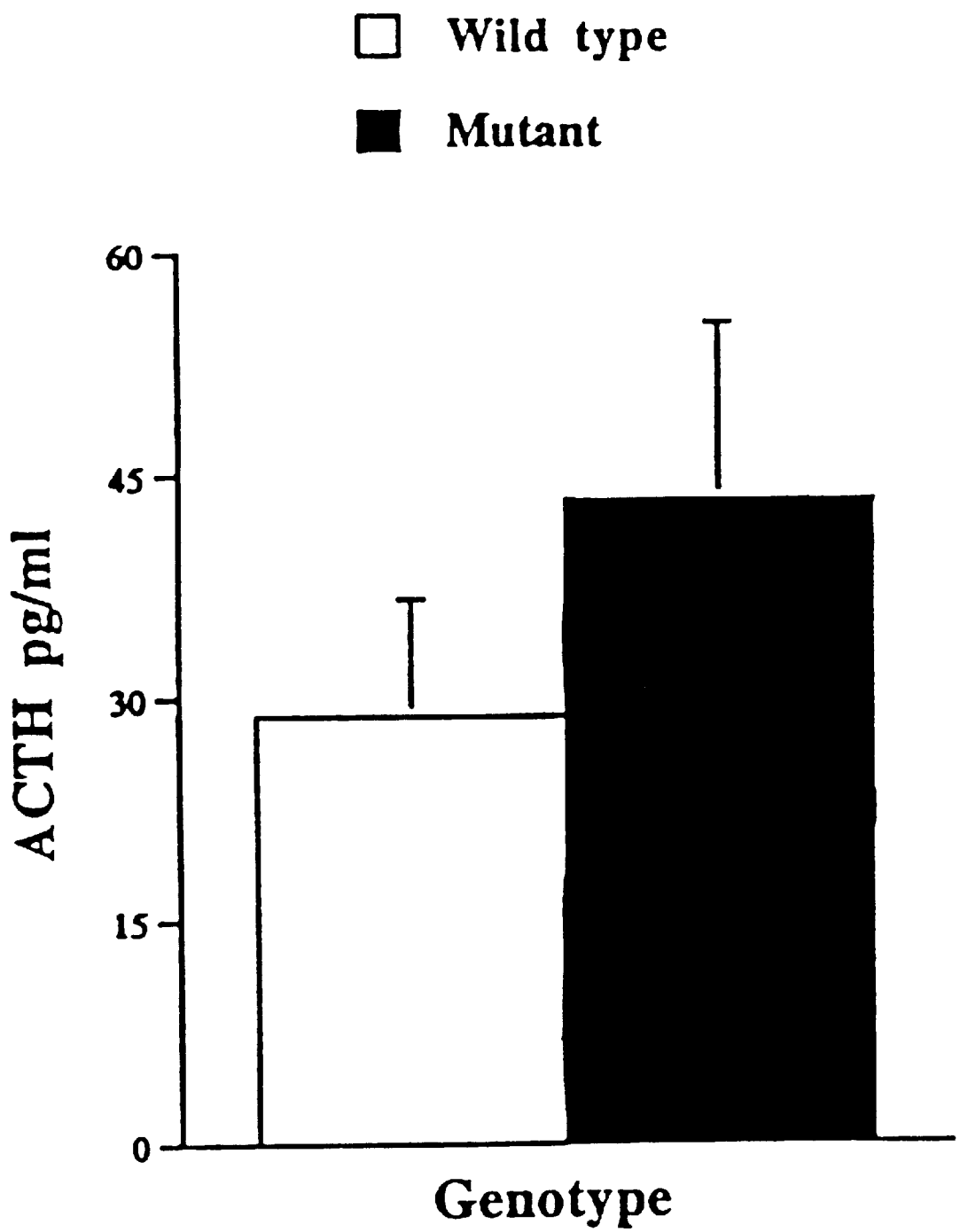
FIGS. 2A–2D demonstrate the hypersensitivity of the HPA axis to stress in mutant animals. *=significantly different from wild type controls at same time point, p<0.01 by Scheffe post-hoc test. Plasma obtained by unanesthetized retro-orbital eyebleeds.
Figure 2B:
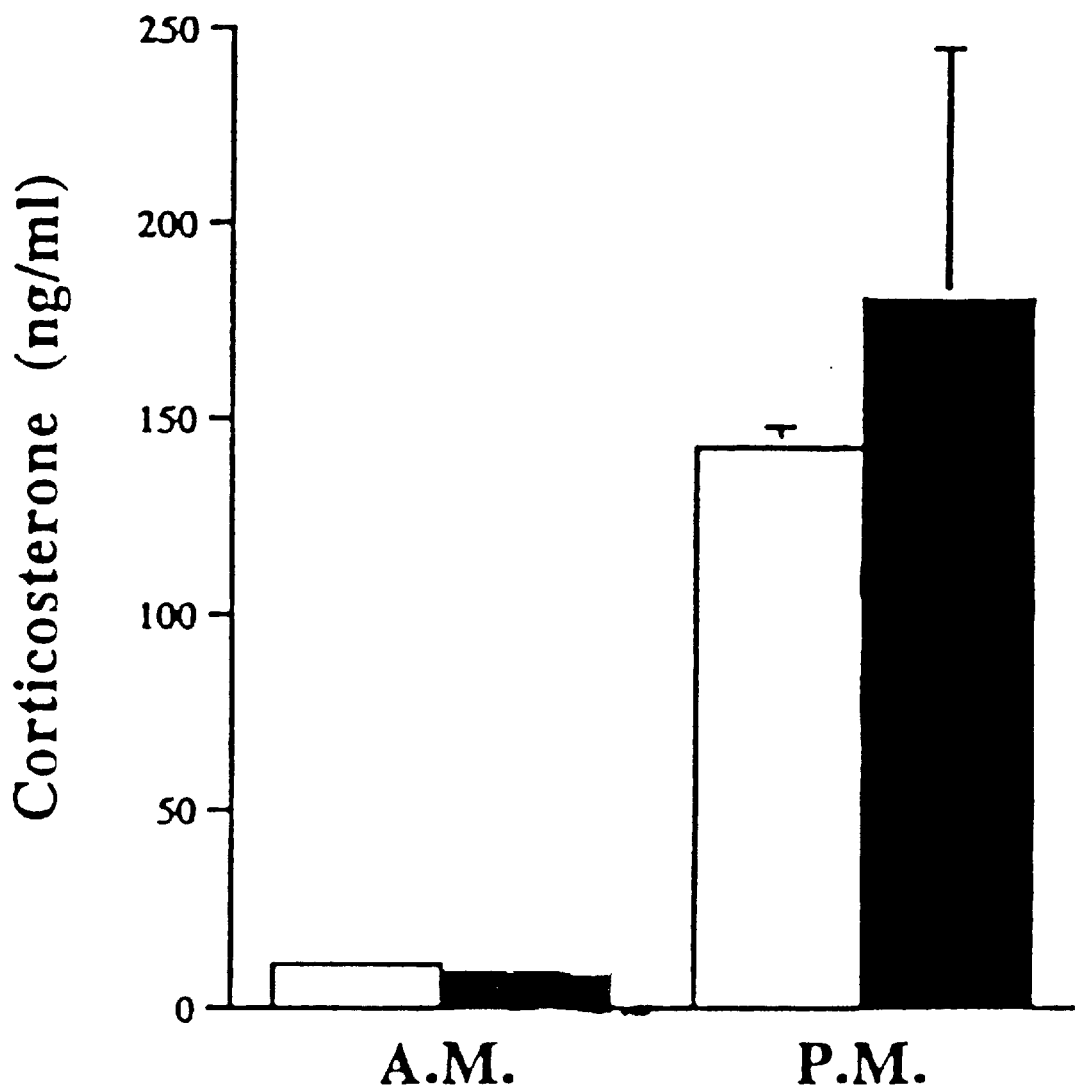

EXAMPLE 4
Determination of Corticosterone and ACTH Levels in CRFR2 Deficient Mice For corticosterone and ACTH analyses, plasma was obtained from individually housed male mice of 10–12 weeks of age. Samples were collected by retro-orbital eye bleed from unanesthetized animals within 30 sec of disturbance of the cage. Basal AM samples were collected at 7:00 AM. Basal PM samples were collected at 5:00 PM. Corticosterone assay (ICN Biomedicals, Dosta Mesa, Calif.) used 5 μl plasma and the ACTH assay (Nichols Institute Diagnostics, San Juan Capistrano, Calif.) used 50 μl plasma as measured in duplicate by radioimmune assay kits. Normal basal levels of ACTH and corticosterone were found in the mutant and control animals (FIGS. 2A–2B), consistent with the finding in FIG. 1E that ACTH levels are unaffected in the brain.

EXAMPLE 5
Effects of Stress on the HPA Axis Response in CRFR2 Deficient Mice In order to examine the HPA axis response to stress, animals were subjected to physical restraint-stress for increasing lengths of time. Blood samples were collected immediately following either 2, 5, or 10 min. of restraint stress in a 50 ml conical tube (plastic conical tube with the bottom removed). Each mouse was bled only once. Plasma samples were immediately centrifuged and stored at −20 C. until the assay was conducted. The Corticosterone assay (ICN Biomedicals, Costa Mesa, Calif.) used 5 μl plasma and the ACTH assay (Nichols Institute Diagnostics, San Juan Capistrano, Calif.) used 50 μl plasma as measured in duplicate by radioimmune assay kits.

Figure 2C:
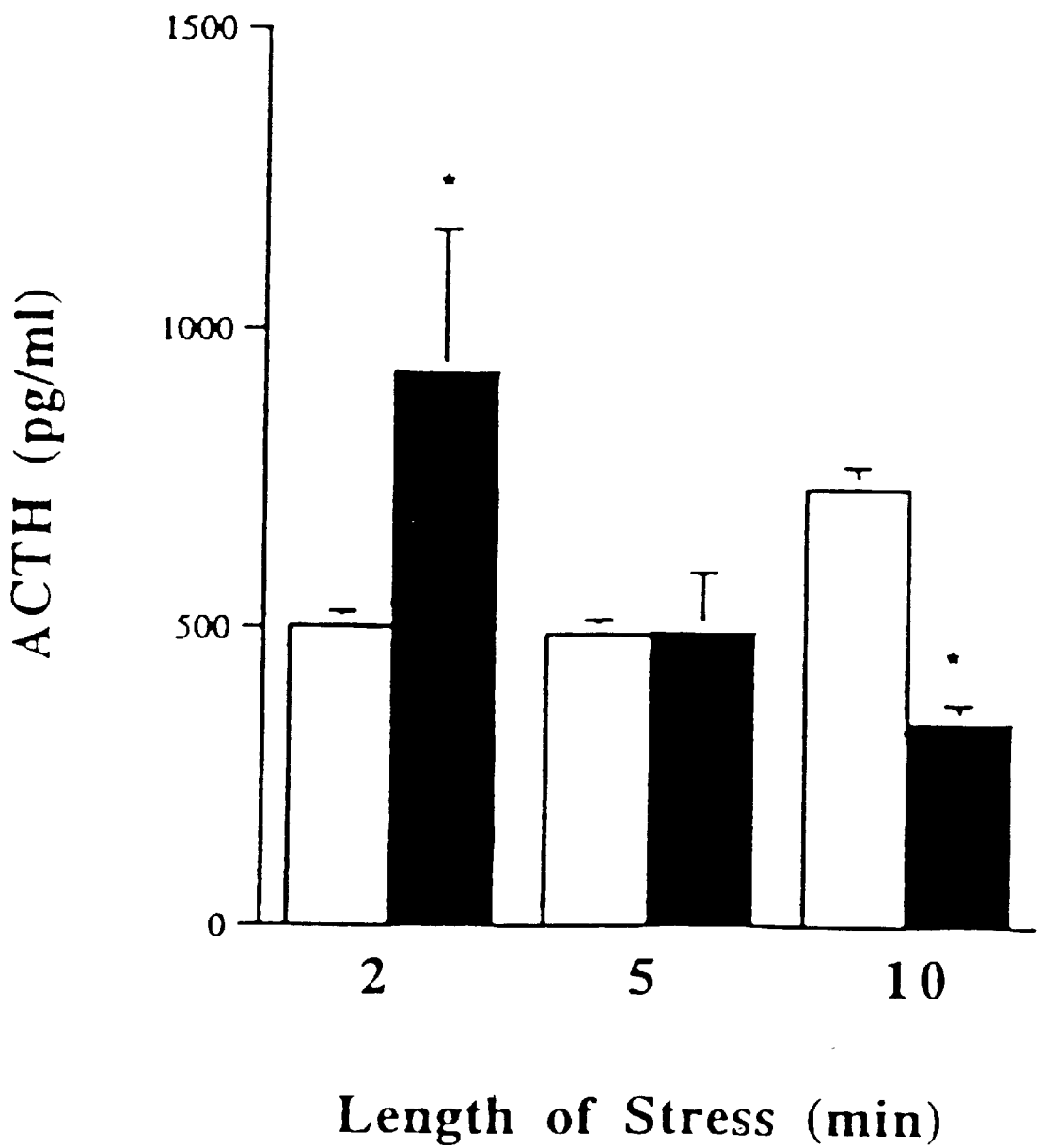
Figure 2D:
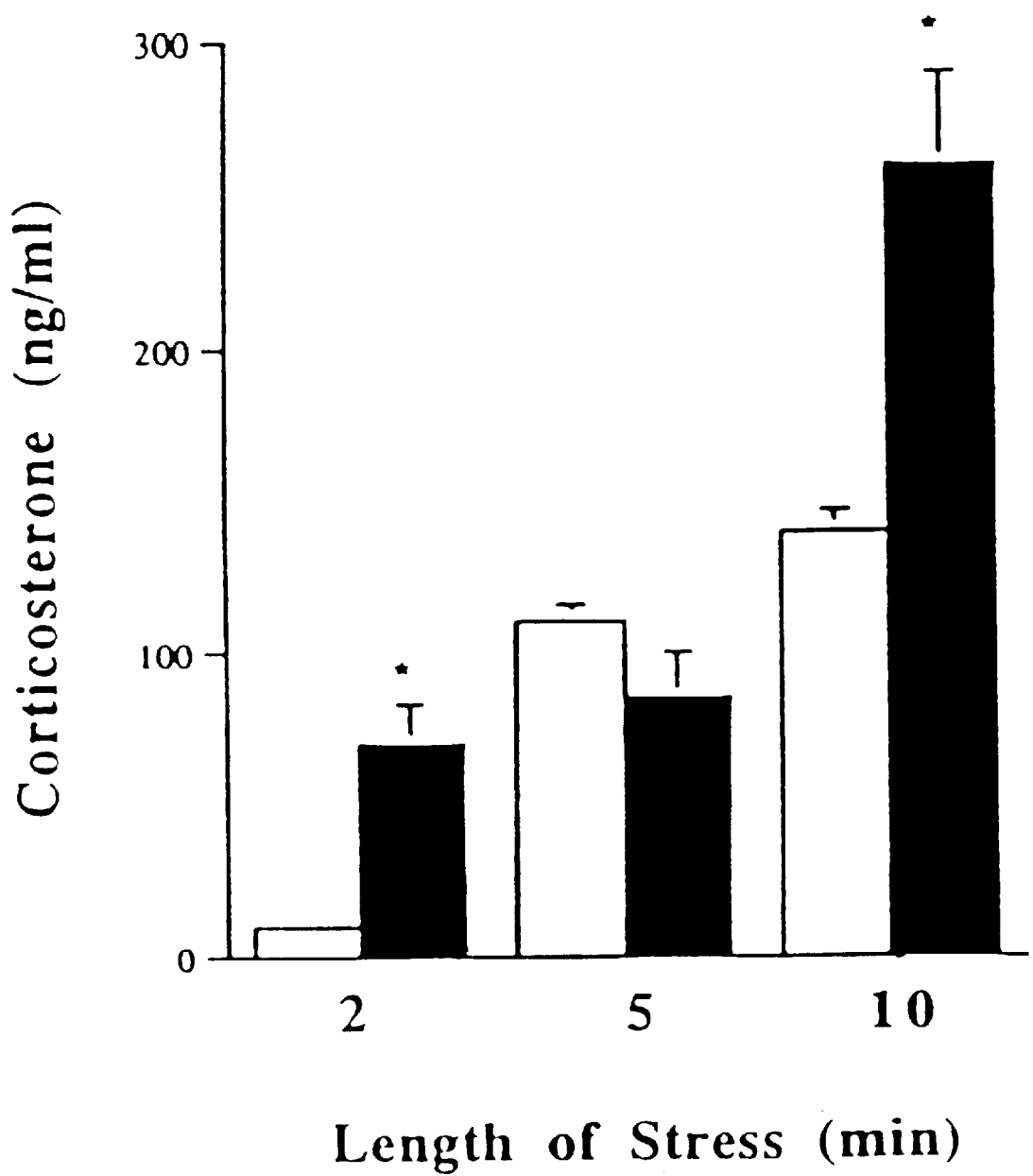

ACTH levels in control animals peaked following ten minutes of restraint. In contrast, ACTH levels in the mutant animals were significantly elevated and peaked following only two minutes of restraint stress (FIG. 2C). Similarly, corticosterone levels in the mutant animals were significantly elevated following two minutes of restraint, whereas control animal levels increased following five minutes of the stress (FIG. 2D). These results demonstrated a hypersensitive response of the HPA axis to stress in the mutant mice.

EXAMPLE 6
CRFR2 Deficient Mice are Sensitive to Food Deprivation

Since CRFR2 is abundant in the VMH and since previous studies had shown an anorectic effect of urocortin (15), basal feeding and weight gain were measured in the mutant and wild type littermates.

Basal feeding was measured in individually housed 12–16 week old male littermates. Mice and their food pellet were weighed daily at 09:00 hrs. For the food deprivation experiment, control and mutant litter mates were individually housed and their basal food intake and weight was established. Mice were food deprived for 24 hrs beginning at 12:00 hrs, but had water ad libidum. Following the food deprivation period, mice were weighed and given a pre-weighed food pellet. Food pellets were then weighed every two hours until lights off (18:00 hrs). Food pellets and mice were again weighed the following morning. Weight loss during the food deprivation, as well as total food consumption and weight gain over the 24 hr period following the food deprivation, were recorded. Basal feeding and weight gain in CRFR2 mutant (mut) male mice were similar to that of wild type (wt) litter mates (24 hr basal food consumption wt=4.3±0.24 g, mut=4.6±0.23 g; body weight wt=21.7±0.66 g, mut=21.2±0.50 g; n=10, averages are ±SEM).

Figure 3A:
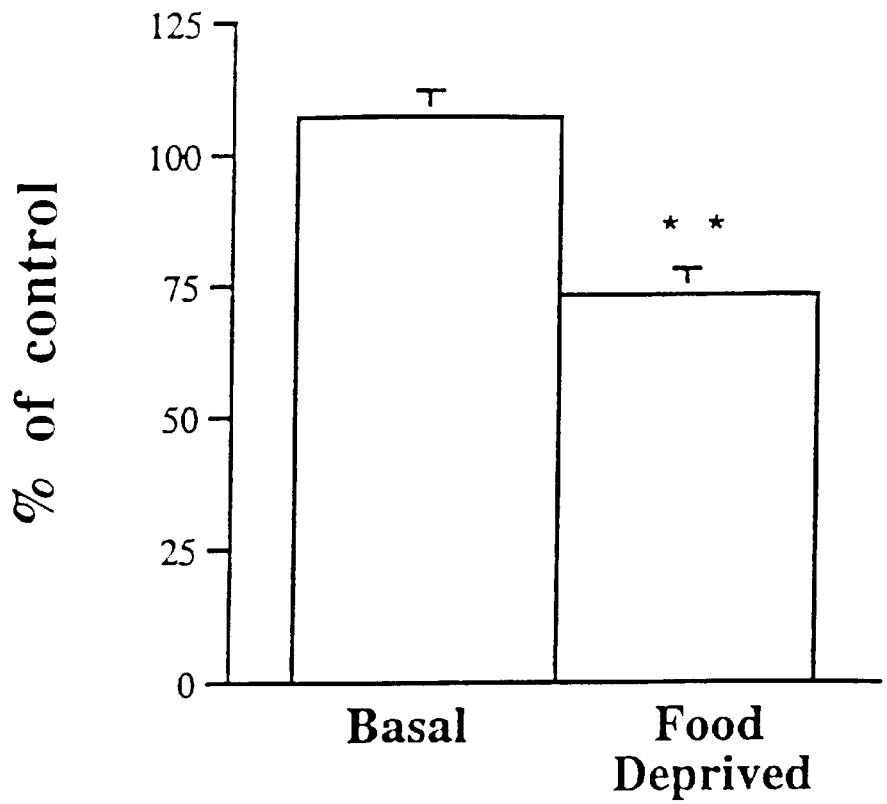
FIGS. 3A–3B show the effects of 24 hours of food deprivation on food intake in wild type and mutant littermate mice.
Figure 3B:
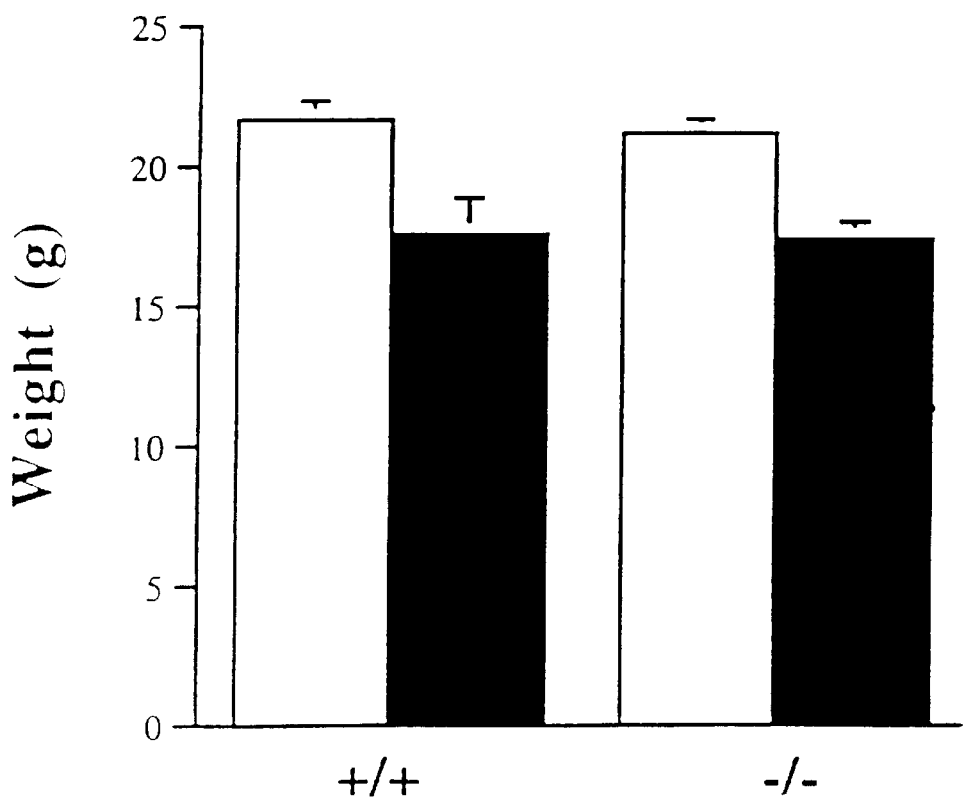

In order to determine if a stressful stimulus would alter the mutant animals' food intake, control and mutant mice were food deprived for 24 hrs and then refed, following which their food intake and weight changes were measured. Food deprivation results showed a significant decrease in food intake in the mutant mice following 24 hrs of food deprivation (FIG. 3A). Mutant mice consumed 75% of wild type food levels in the 24 hr period following the food deprivation. However, the mutant and wild type body weights were not significantly different following food deprivation or refeeding (FIG. 3B).

EXAMPLE 7
Evaluation of Anxiety-like Behavior in CRFR2 Deficient Mice in Elevated Plus Maze Since CRFR1 mutant mice displayed anxiolytic-like behavior (10), CRFR2 mutant mice were analyzed in similar tests using three different test paradigms. In the first test paradigm, control and mutant animals were evaluated using the elevated plus maze (EPM). Male and female mice between 22–24 weeks of age were used in this experiment. Wild type littermate mice were used as the controls. Animals were group housed, maintained under regular light/dark conditions (lights on 6:00 AM, lights off 6:00 PM), and handled on alternate days one week prior to testing.

The plus maze apparatus was made of black Plexiglas and had two open arms (30×5 cm) and two enclosed arms of the same size with walls 30 cm high. It was elevated 30 cm above the ground. The arms were connected by a central square (5×5 cm) and thus the maze formed a plus sign. A 25 watt lamp placed above the apparatus provided a 6 lux light level in the open arms. All testing was performed during the light phase of the light-dark cycle. Mice were habituated to the experimental room conditions for 1 hour prior to the behavioral testing and the subjects were individually tested in 5-min sessions.

Each mouse was placed on the center platform facing an open arm to initiate the test session. Behaviors scored were the number of open and closed arm entries and the amount of time spent on the various sections of the maze. Arm entries were defined as an entry of all four paws into the arm. Closed arm entries were taken as an index of locomotor activity in the plus maze. A camera mounted above the apparatus allowed the observation of animal behavior on a video monitor placed in an adjacent room. At the end of the test, the number of entries into and the time spent on the open arms were expressed as a percentage of the total number of arm entries and test duration, respectively. Results are expressed as the mean ± standard error of the mean. Behavioral parameters obtained from the EPM test were analyzed using the Student's t test.

Figure 4A:
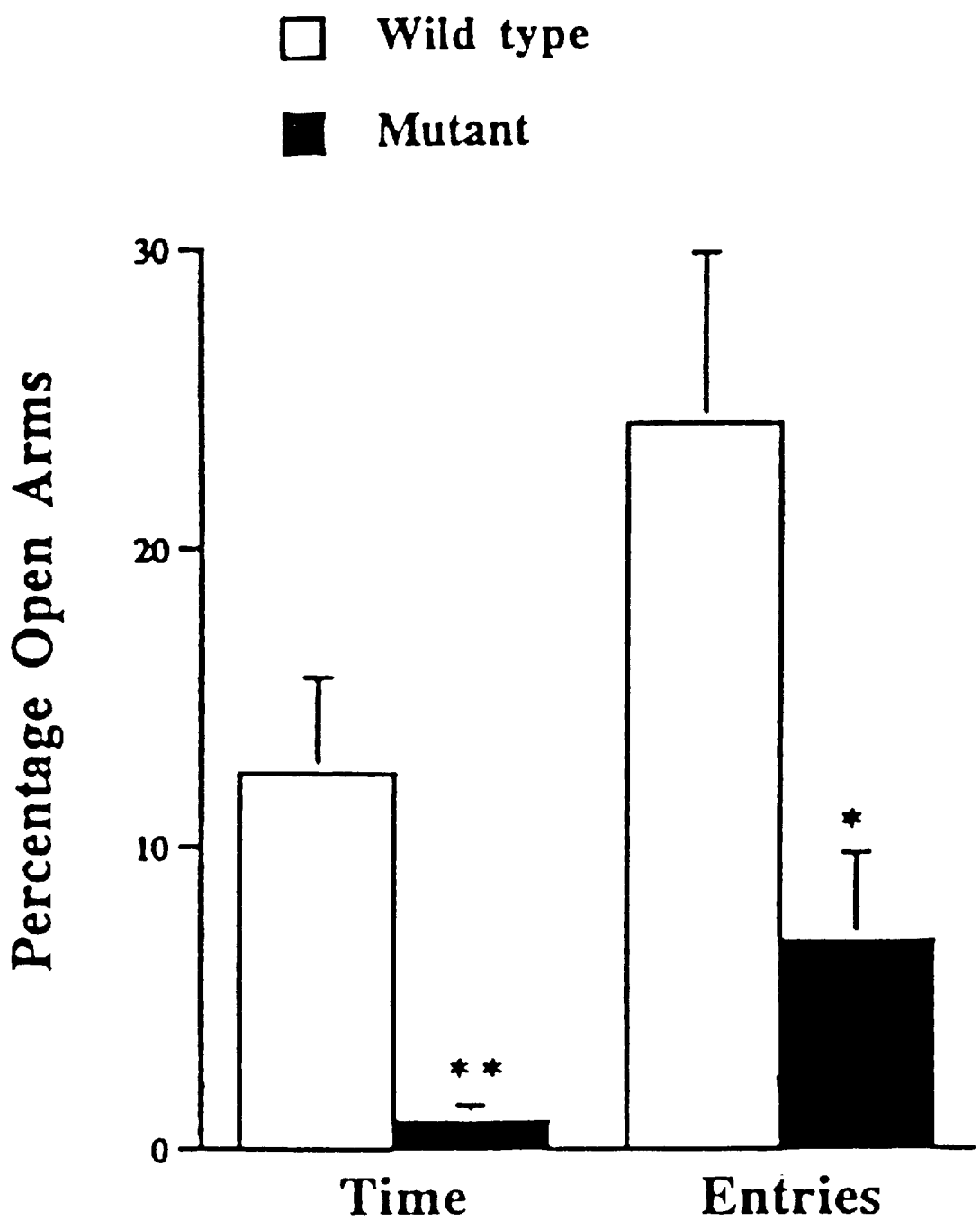
FIGS. 4A–4H demonstrate the increased anxiety-like behavior of mutant animals in the elevated plus maze and open field test.
Figure 4B:
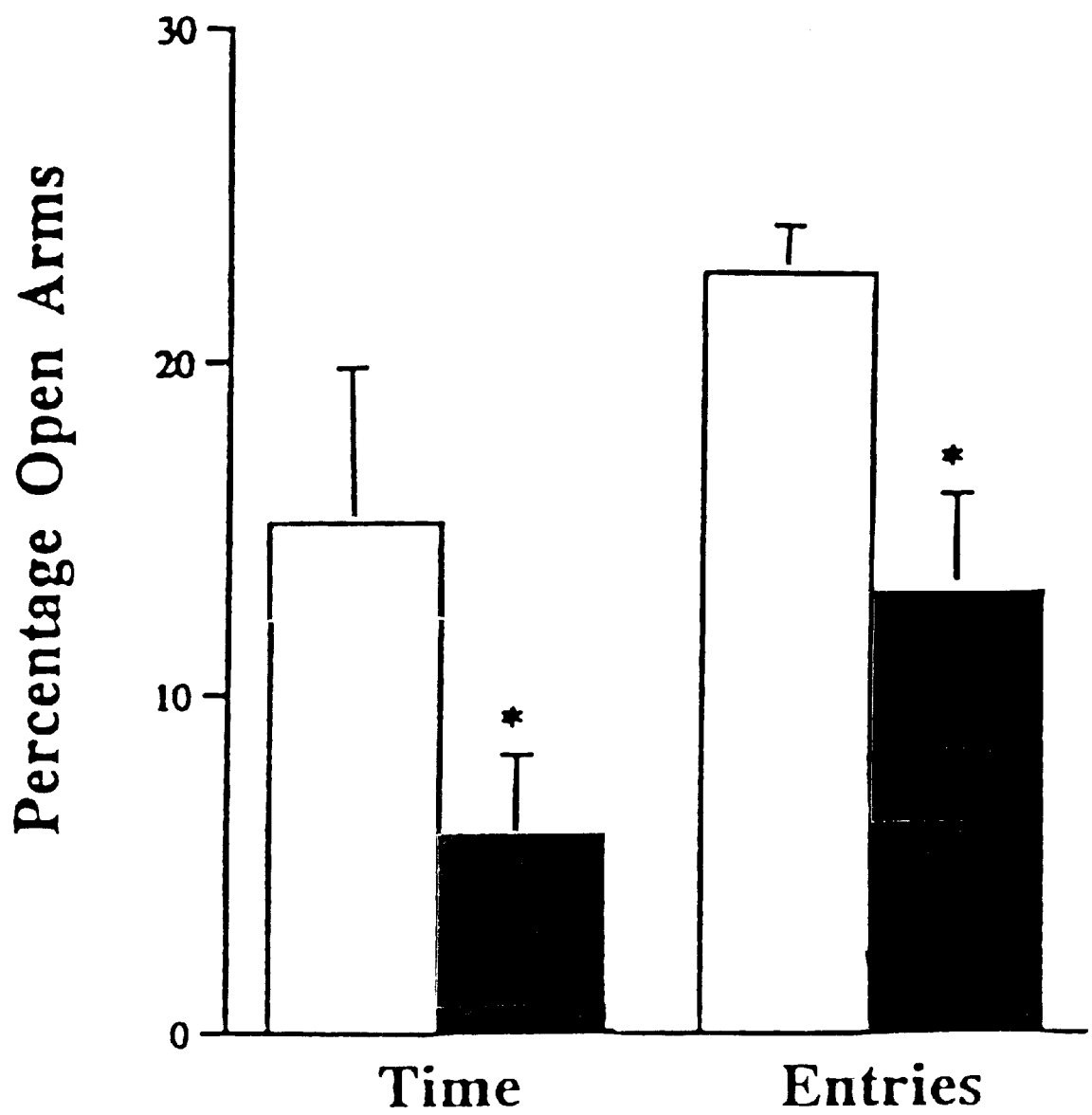
Figure 4C:
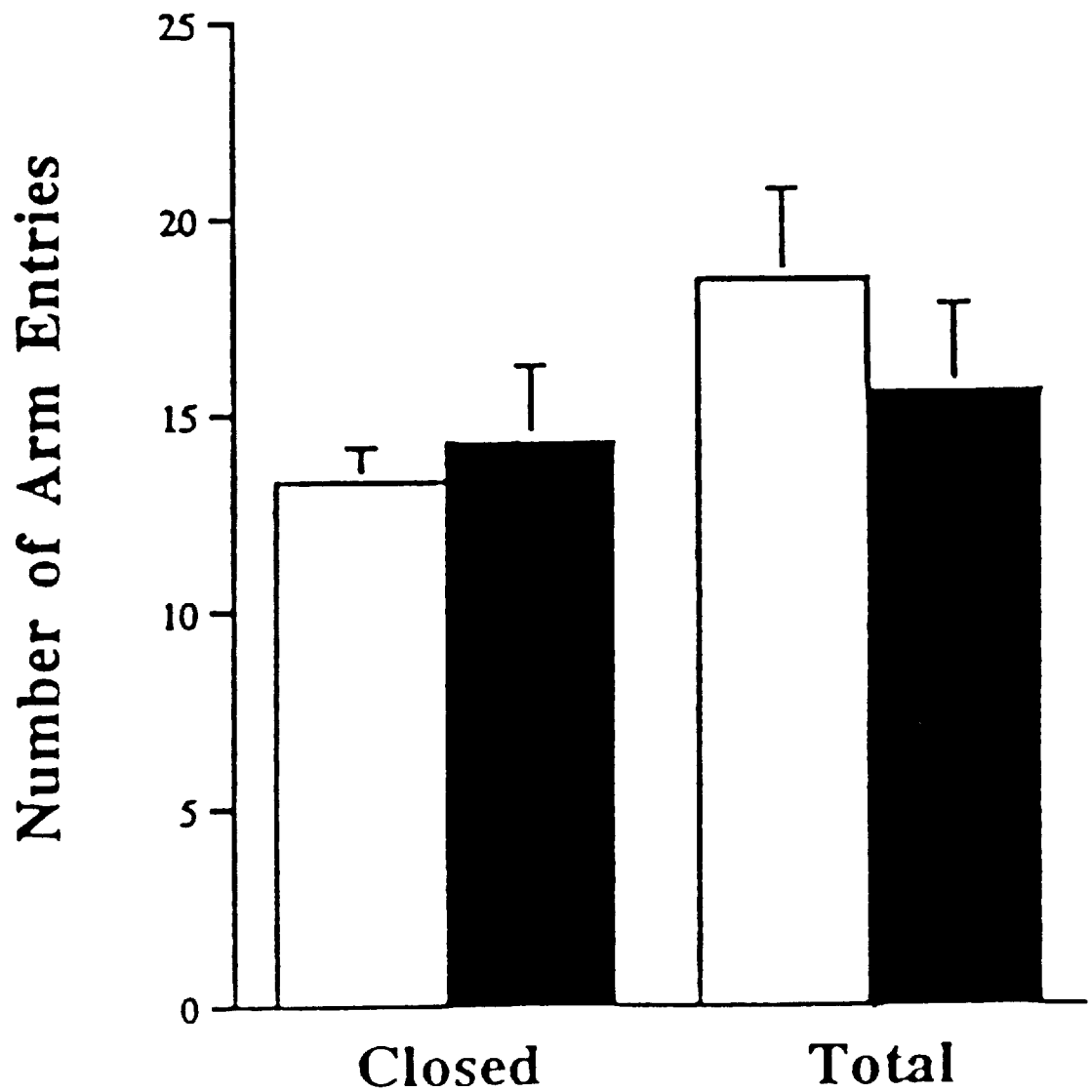
Figure 4D:
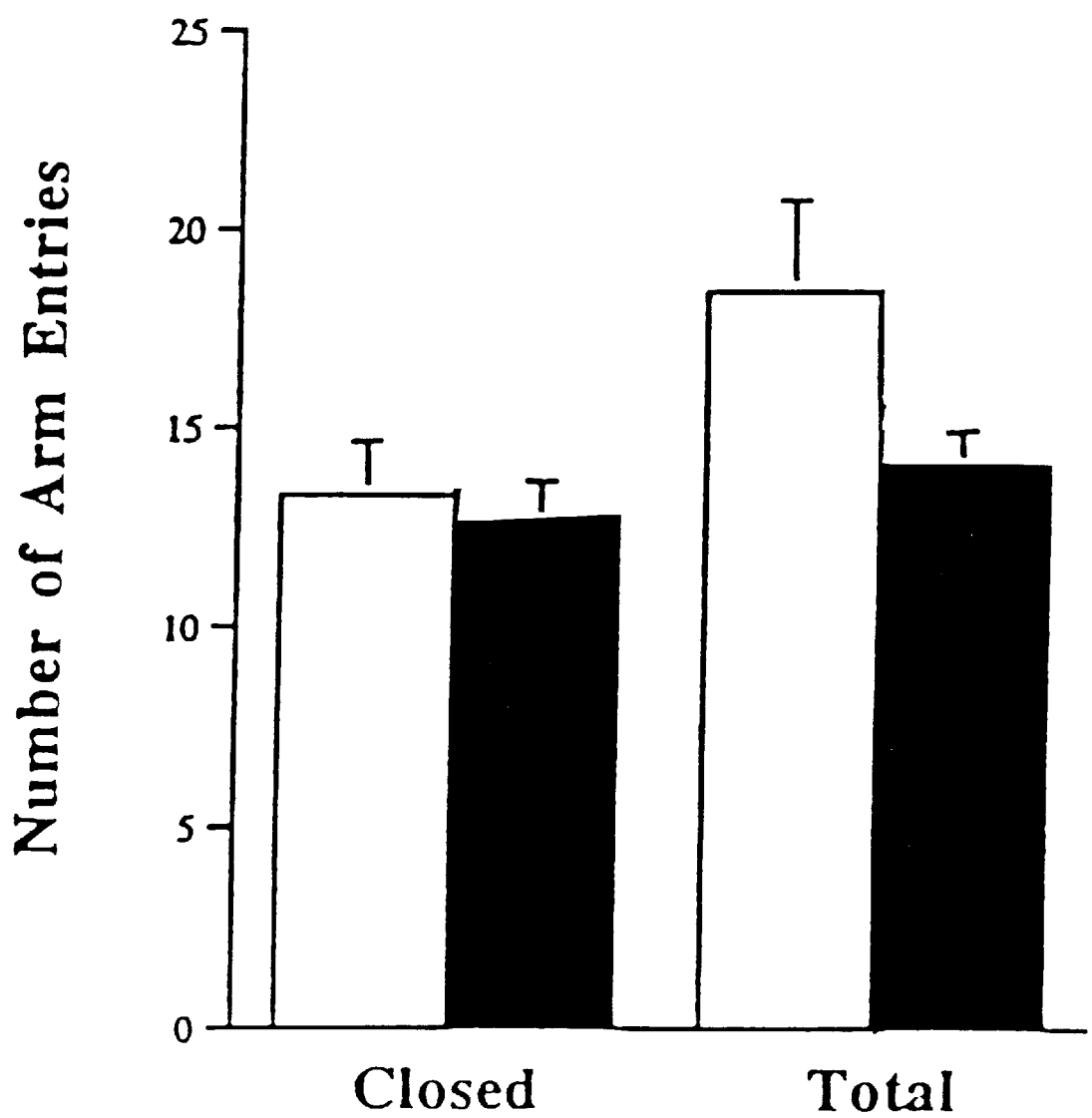

Results showed that both male and female CRFR2 mutant mice spent less time on and entered less frequently the open arms of the plus-maze apparatus than did the wild type controls. A significant effect was found for both percent entries into the open arms for both male and female mice (FIGS. 4A and 4B). The increase in anxiety-like behavior was not due to altered locomotor activity, as overall activity in closed arm and total arm entries was not different between the two groups (FIGS. 4C and 4D). These results demonstrate that CRFR2 mutant mice exhibit markedly increased anxiety-like behavior.

EXAMPLE 8
Evaluation of Anxiety-like Behavior in CRFR2 Deficient Mice in a Light/dark Box The behavior of CRFR2 mutant and control mice was also analyzed for anxiety-like behavior in a light/dark box. A rectangular, plexiglass box was divided into two compartments, one painted white (28.5 cm×27 cm) and one painted black (14.5 cm×27.0 cm). Light intensity was 8 lux in the black compartment covered by a red plexiglass lid and 400 lux in the white compartment. The compartments were connected by an opening (7.5 cm×7.5 cm) located at floor level in the center of the partition. All testing was done during the dark phase of the cycle, between 19:00 hrs and 21:00 hrs. Each animal was tested for 10 min by being placed in the center of the white area and the number of transitions between the two compartments and the amount of time spent in the white area was recorded. A camera mounted above the apparatus allowed for observation and recording from an adjacent room.

Figure 4E:
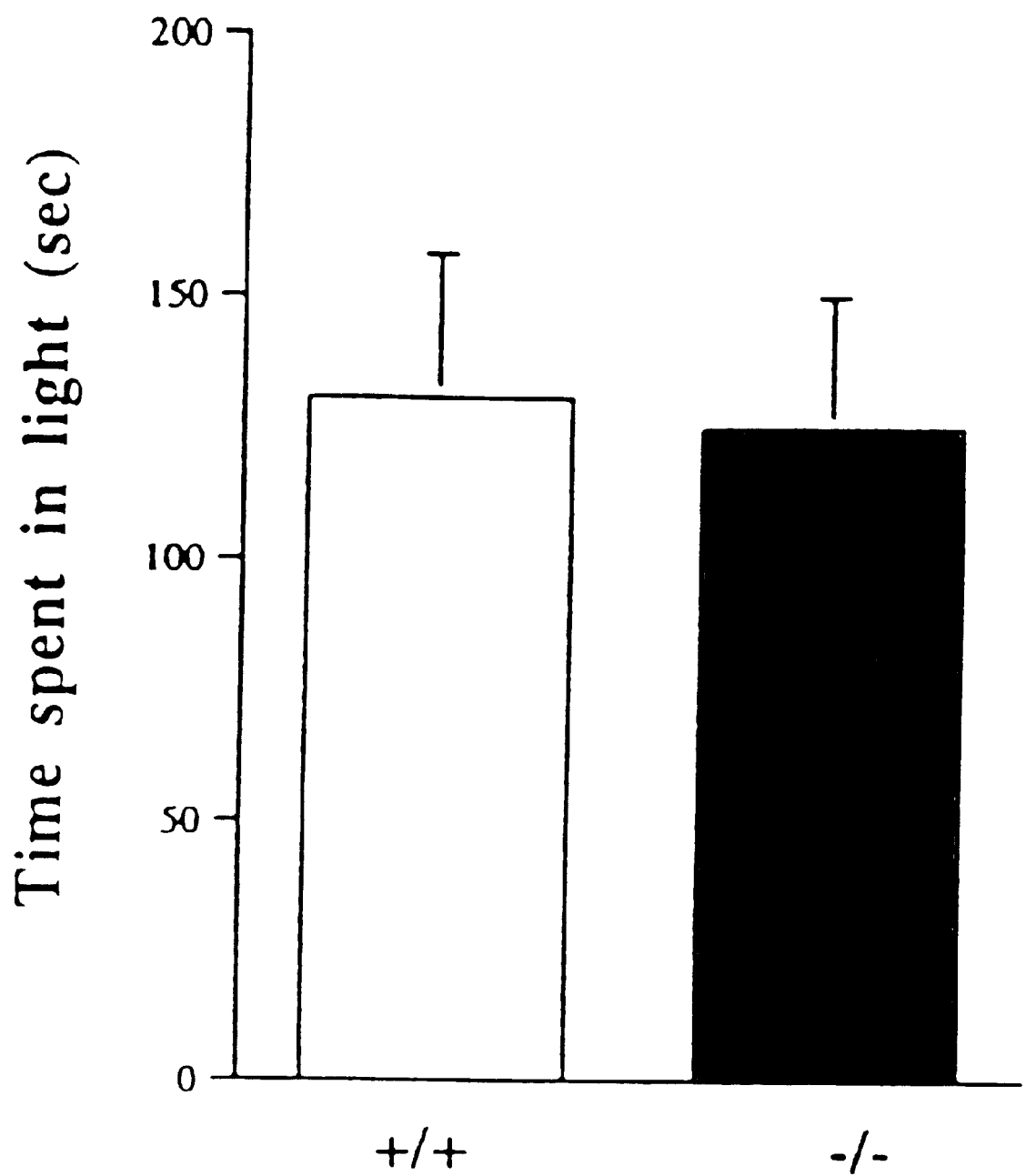
Figure 4F:
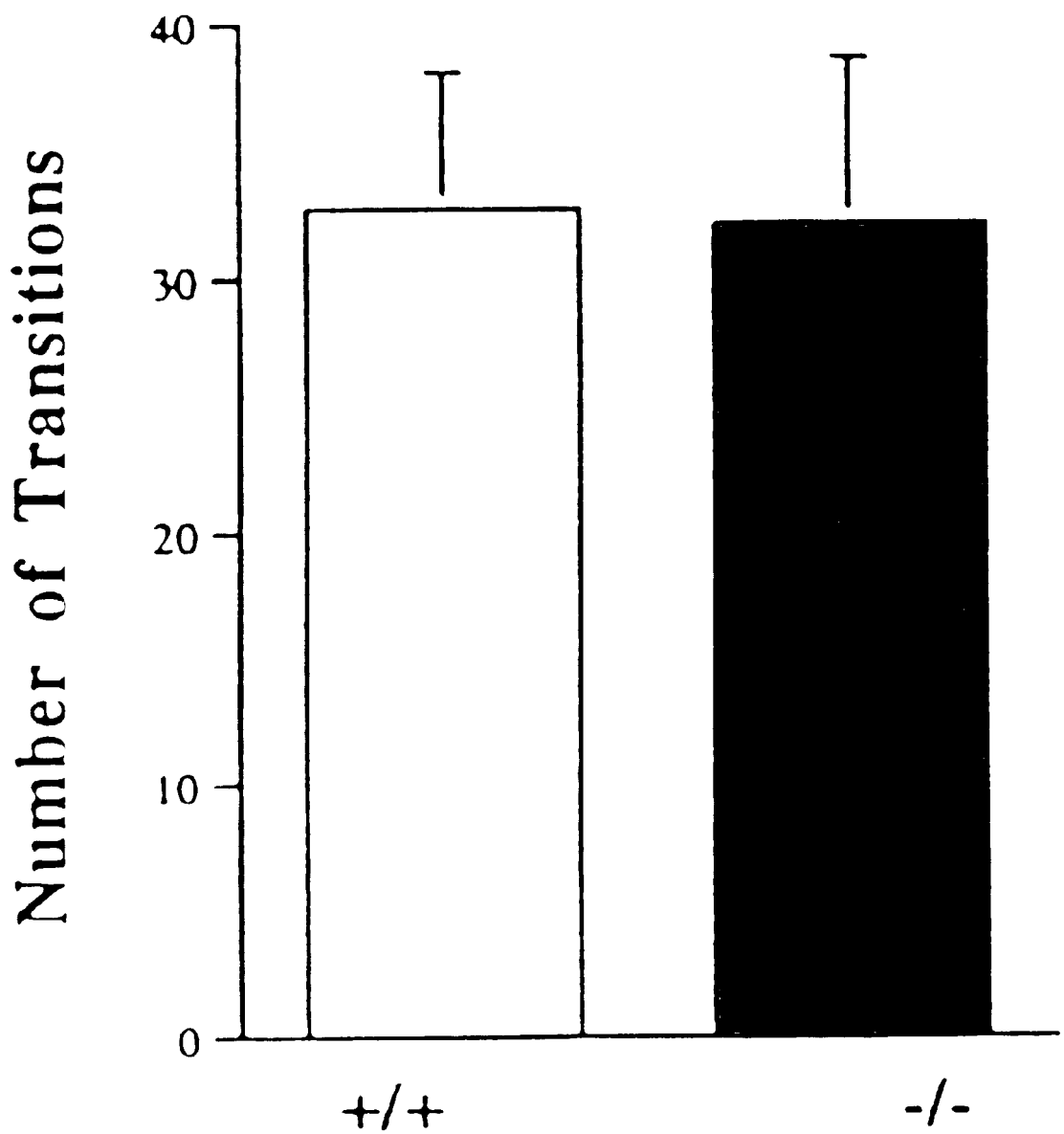

Results from the Light/Dark box demonstrated that CRFR2 mutant mice spent as much time in the light portion of the box and had as many transitions between the light and dark portions of the box as control mice (FIGS. 4E&4F). No significant differences were detected between the two groups in this experiment.

EXAMPLE 9
Evaluation of Anxiety-like Behavior in CRFR2 Deficient Mice in an Open Field Test Anxiety-like behavior was also analyzed in CRFR2 mutant and control mice in an open field apparatus. The open-field apparatus consisted of a white plexiglass box (50×50×22 cm) with 16 squares (12×12 cm) painted on the floor (12 outer and 4 inner). A lamp directed to the center of the field provided a 120 lux illumination on the floor. Testing was conducted during the dark phase of the light-dark cycle in a room with constant background white noise (52 dB). Each mouse was placed in the center of the apparatus to initiate a 10-min test session. Time (sec) spent in the inner squares, ambulation (number of squares crossed), defecation (number of fecal boli), rearings, and time spent grooming (sec) were quantified from a video recording. Inner square crossings were also expressed as a percentage of ambulation.

Figure 4G:
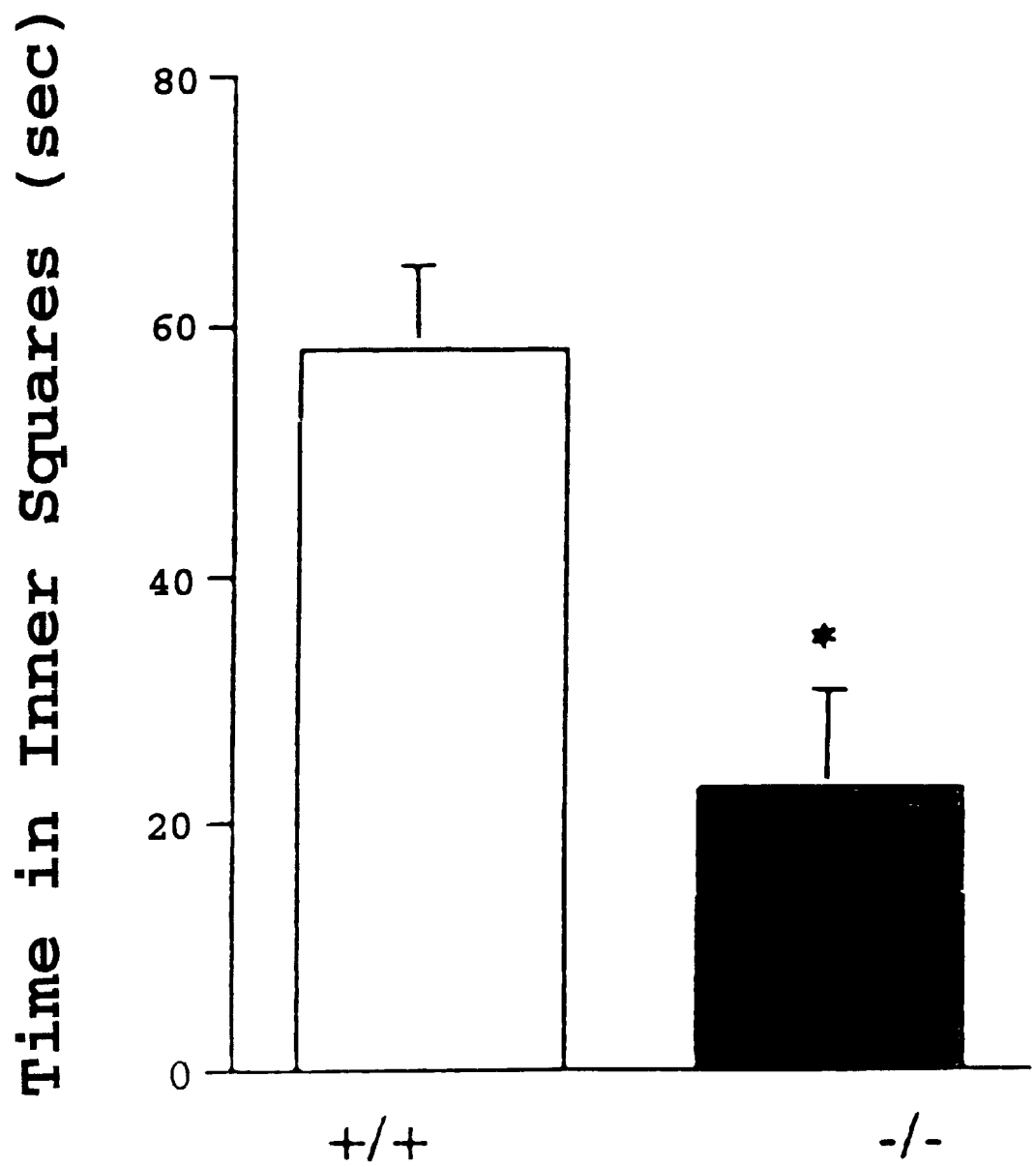
Figure 4H:
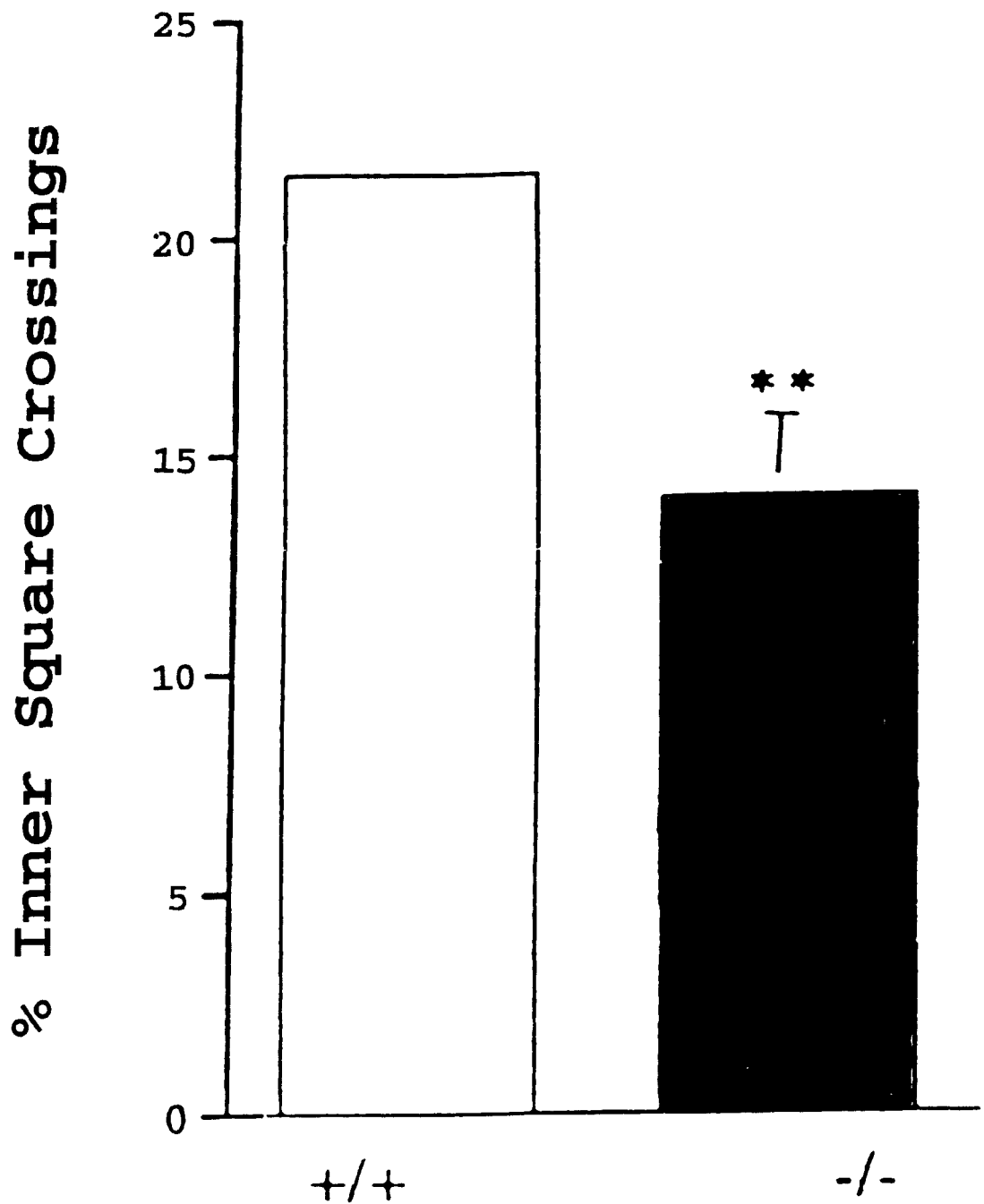

The results from the open-field test showed that the CRFR2 mutant mice spent less time in and displayed a lower percentage of inner square crosses than did wild type mice (FIGS. 4G&H). No differences in ambulation, rearings, defecation, or grooming were observed between the groups (data not shown).

EXAMPLE 10
Effect of CRFR2 Deficiency on the Expression of Other Genes

As no gross anatomical defects were detected in components of the HPA axis (FIGS. 1D & 1E), the alterations in stress and behavioral responses in the mutant animals may be due to altered gene expression of other components of the CRF signaling pathway. To investigate this possibility, expression of UCN, CRF, and CRFR1 mRNAs were examined by in situ hybridization.

In situ hybridization was performed according to methods described previously (36). Briefly, tissue sections (20 μm) were fixed in 4% paraformaldehyde, rinsed in PBS, immersed in acetic anhydride, dehydrated through a series of graded ethanol, delipidated in chloroform, and again dehydrated. Slides were then hybridized with an $^{35}$S-labeled riboprobe in a 50% deionized formamide hybridization mix overnight at 55° C. in a humidified incubation chamber. Following the incubation, slides were washed in 1×SSC at room temperature for 30 minutes with shaking, treated with 20 μg/ml RNase (Promega) at 37 C. for 30 min., rinsed in 1×SSC buffer at room temperature for 30 minutes, washed 3× for 20 minutes at 65 C. in 0.1×SSC with shaking, rinsed in 0.1×SSC at room temperature for 30 minutes, dehydrated in a series of graded ethanols, air dried, and apposed to Kodak hyperfilm (Eastman Kodak, Rochester, N.Y.) for three days.

After films were developed, slides were dipped in NTB2 liquid nuclear emulsion (Eastman Kodak; diluted 1:1 with water), exposed for 10 days, photographically processed, counter-stained with hematoxylin, and coverslipped. Slides were analyzed using the image analysis system Image Pro Plus (Media Cybernetics, Silver Springs, Md.). For analysis of the PVN and cAmyg, a circle tool (area=3022 pixels) was used to determine mean optical density for each section such that anatomically atlas matched sections for each animal were compared in the identical region of the PVN and cAmyg. The EW cell bodies expressing urocortin were too diffuse to analyze using standard optical density methods. Therefore, parameters were used such that the computer determined the number of cells within the designated EW expressing a minimum optical density by color and cell size as predetermined to exclude non-positive cells and background silver grains. Each cell determined to be positive by the computer for urocortin mRNA was then also counted for optical density. The average optical density and cell number for each section was then compared.

Figure 5A:
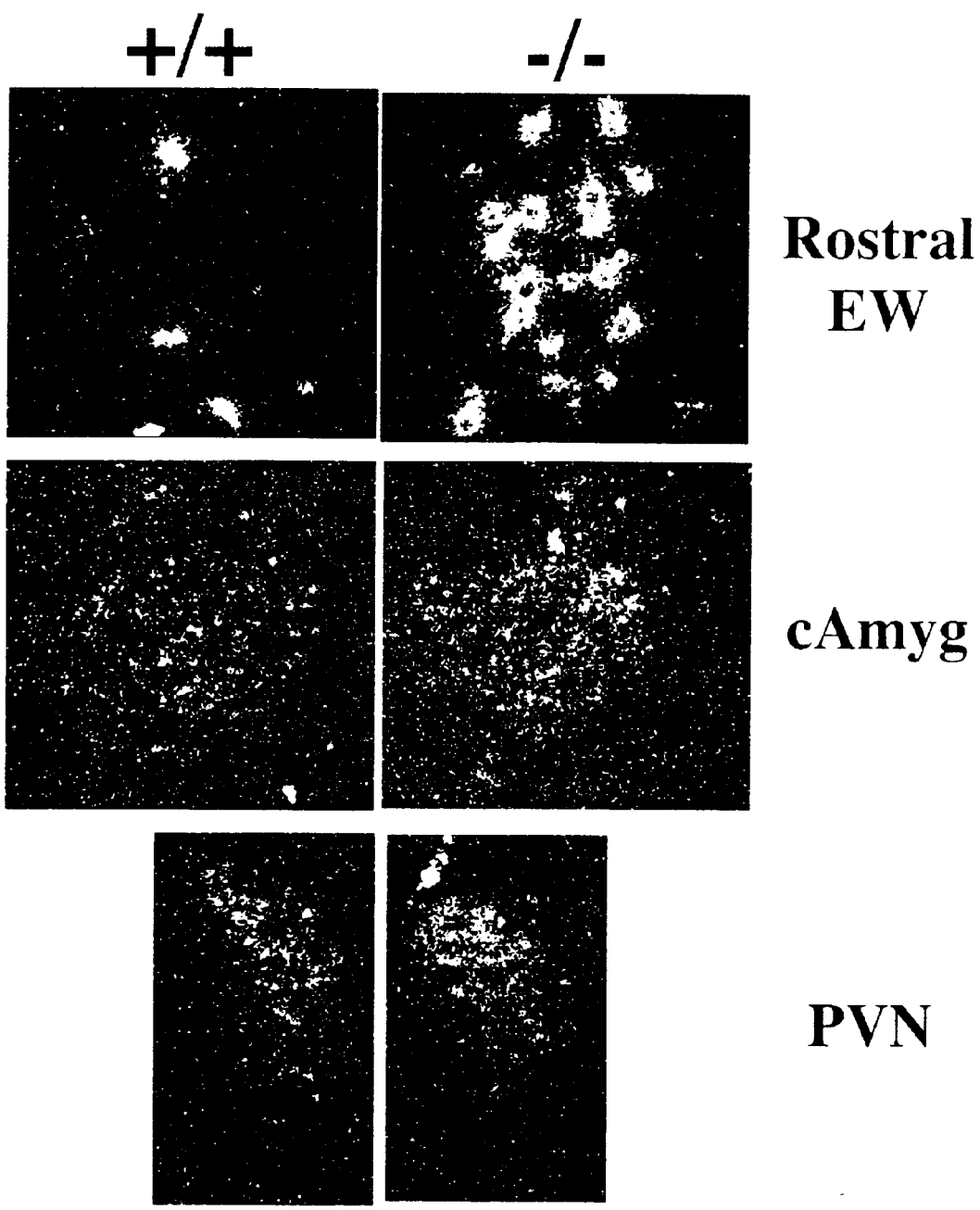
FIGS. 5A–5E show increased levels of urocortin and CRF mRNA in the mutant brains. For 5B to 5E, all numbers were the average of n=3 for mutant and wild type mice, +SEM, *, p<0.05; p<0.01; *, p<0.005, by Fischer's PLSD post-hoc test.
Figure 5B:
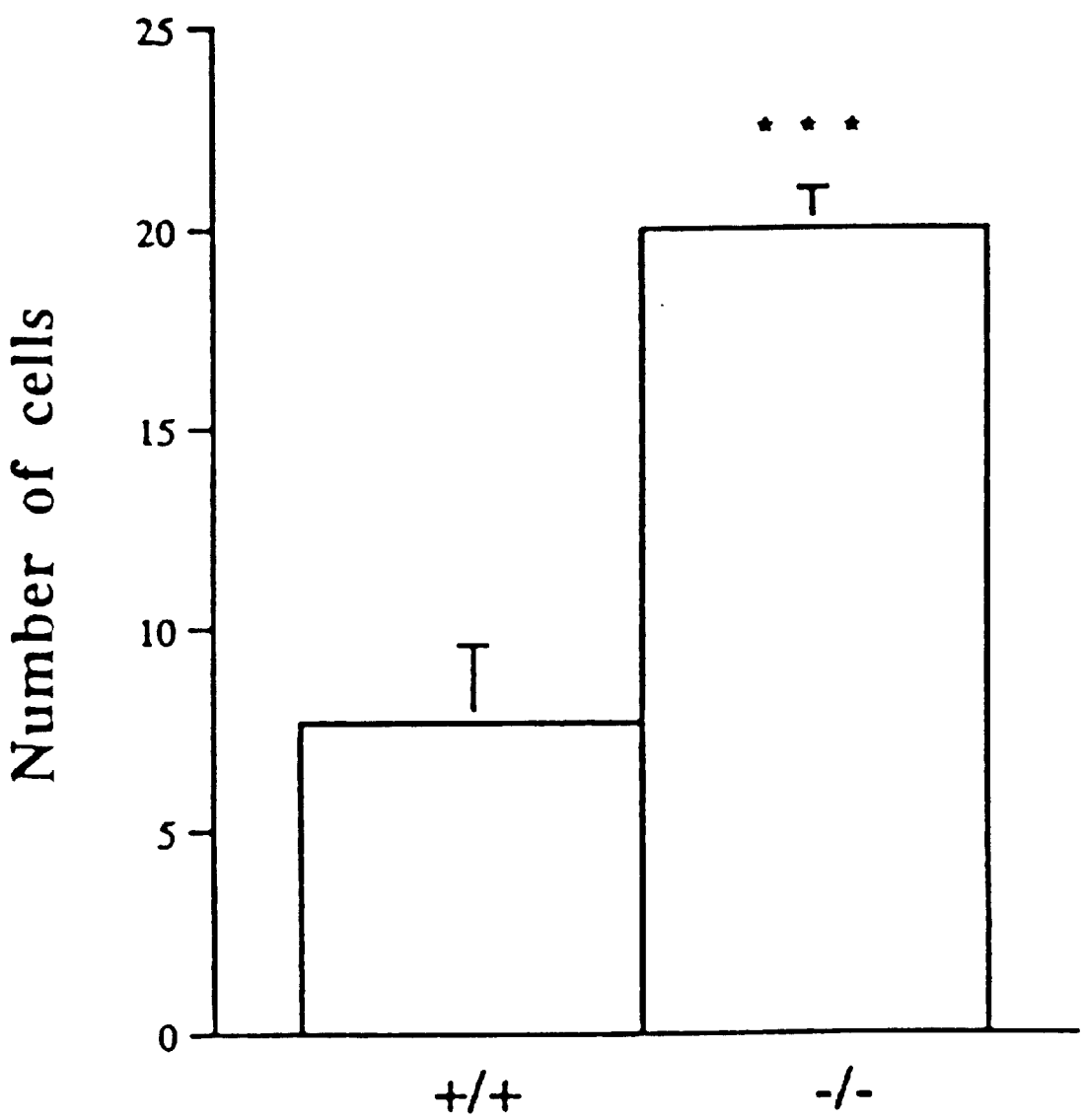
Figure 5C:
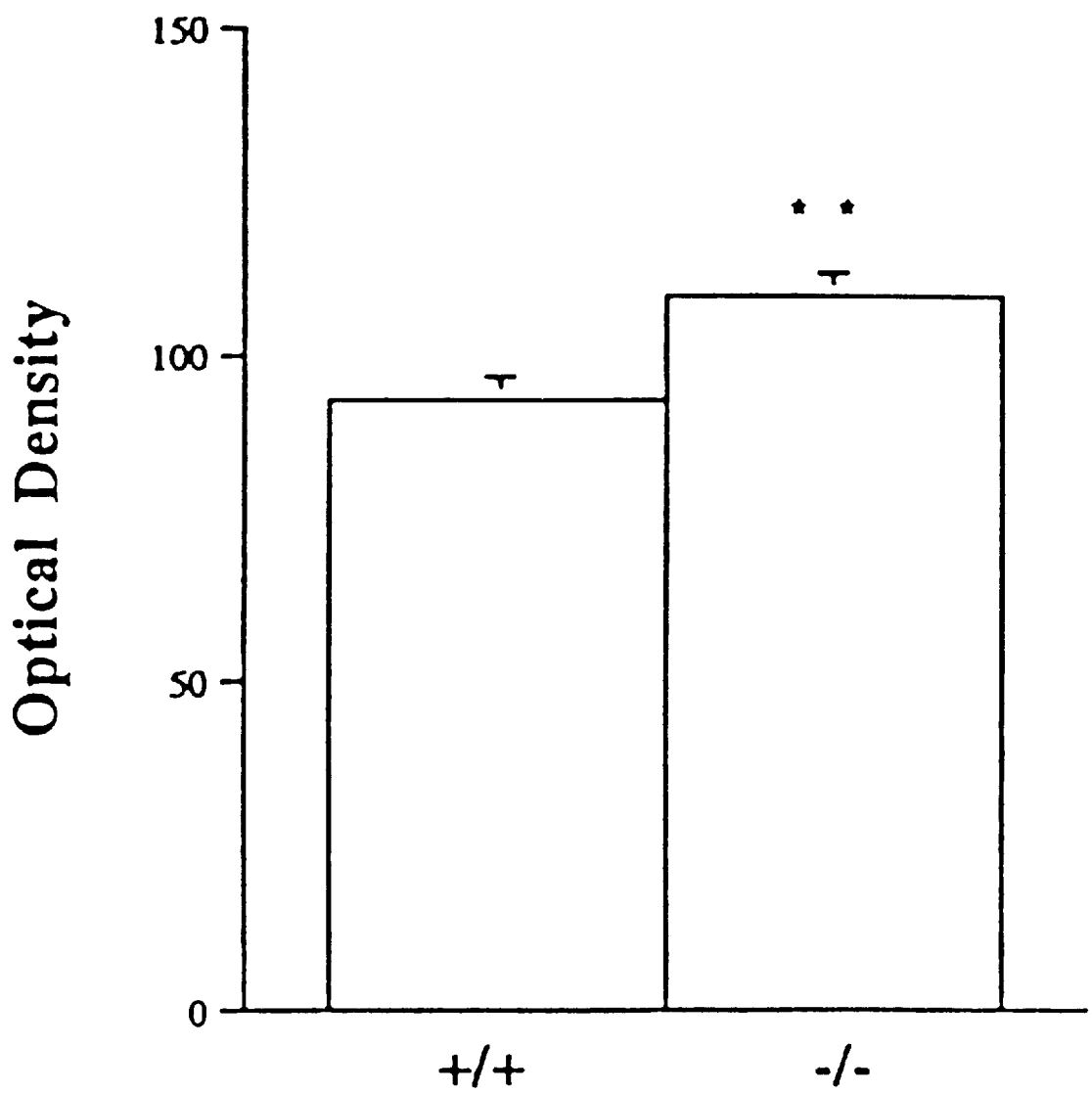
Figure 5D:
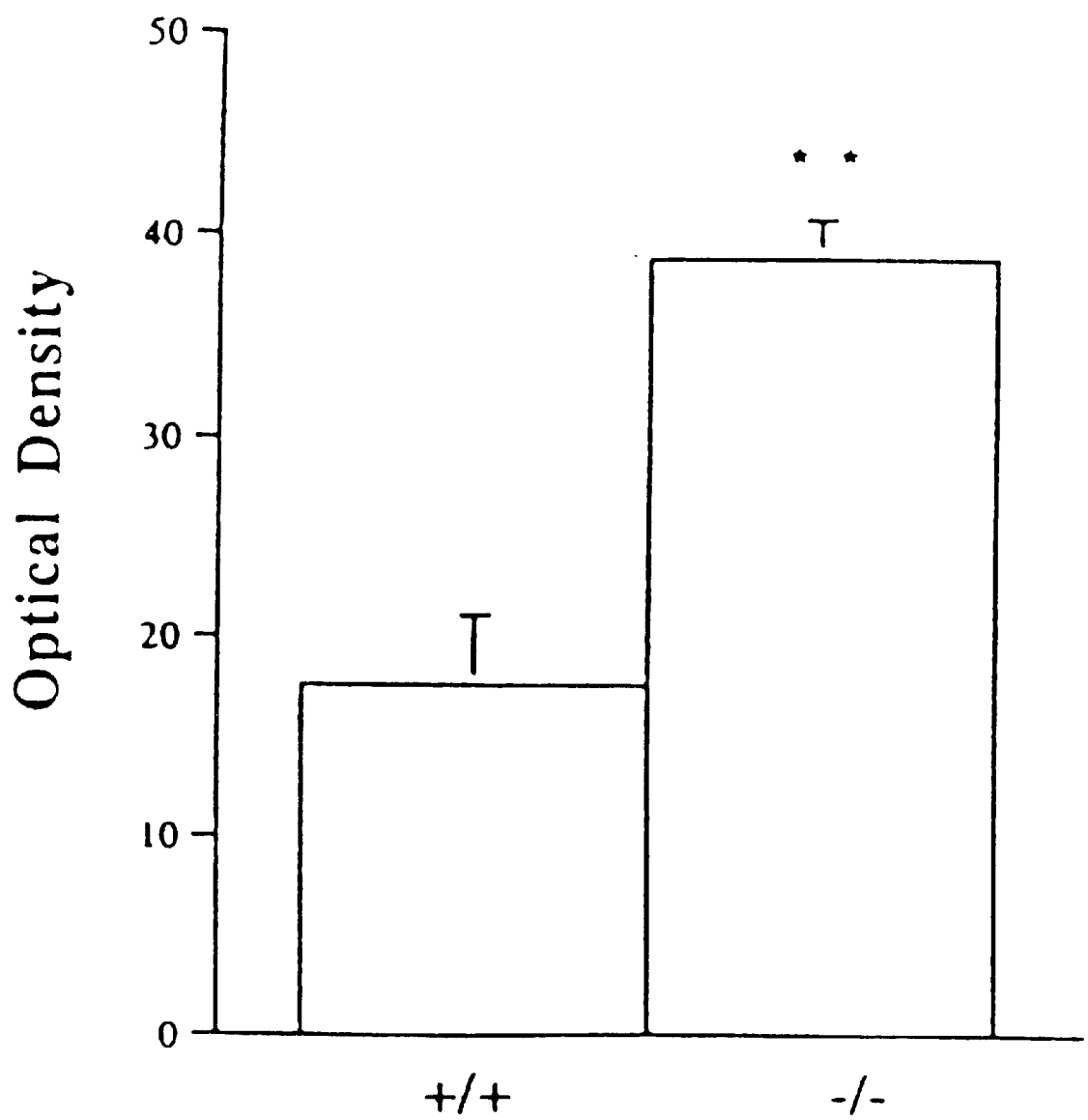
Figure 5E:
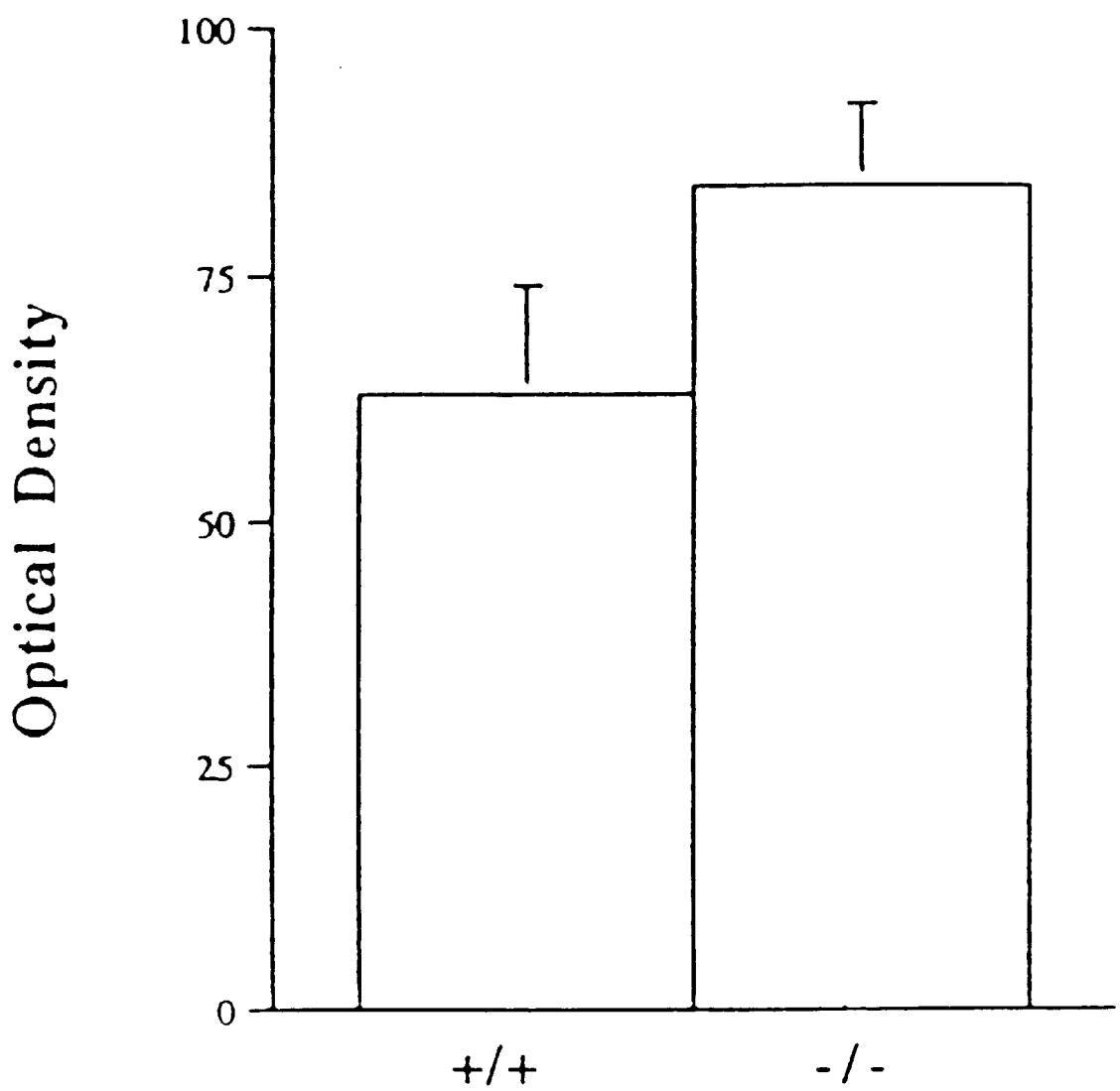

As illustrated in FIG. 5A, urocortin mRNA was significantly increased in the rostral region of the Edinger Westphal (EW) nucleus for both the number of cells expressing (FIG. 5B) as well as in the density of urocortin mRNA per cell (FIG. 5C) in the mutant animals. The central nucleus of the amygdala (cAmyg) showed a significant increase in CRF mRNA in the null mutant animals (FIGS. 5A & 5D). No significant change in CRF mRNA in the PVN was detected in basal, nonstressed animals (FIGS. 5A & 5E). The expression patterns or levels of CRFR1 mRNA in the brain or anterior lobe of the pituitary gland did not differ between the mutant and wild type mice (data not shown). These results show that CRFR2 mutant mice have increased expression levels of CRF mRNA in the cAmyg and urocortin mRNA in the rostral Edinger Westphal nucleus.

EXAMPLE 11
Evaluation of Hypotension in Response to UCN in CRFR2 Mutant Mice Previous reports have shown hypotension in response to a peripheral injection of urocortin (2). Additionally, CRFR2s have been localized to the vascular endothelial cells (5, 8) and have been hypothesized to be responsible for the vasodilatory action of urocortin. In order to test this hypothesis, CRFR2 mutant and control mice were injected with urocortin and the alteration in their blood pressure was measured.

The cardiovascular responses to intravenous infusion of urocortin and sodium nitroprusside, a vasodilator, were examined in mice (wild type: n=5; mutant: n=3) anesthetized with isofluorine. The arterial catheter for blood pressure recording was fabricated from a sterile PE-10 tubing softened and pulled to an outer diameter of ~0.4 mm. The femoral artery was exposed, and the arterial catheter filled with heparin saline (500 U/ml) was implanted and secured with surgical threads and tissue glue (Vetbond). The catheter was connected to a blood pressure transducer (Statham), and the arterial pressure pulses were displayed on a Gould pen-recorder. A second catheter was then implanted in the external jugular vein for intravenous infusion of drugs. Drug infusion was performed 30 min following completion of the cannulation procedure. The venous catheter was connected to a drug-filled syringe. Infusion was completed within 0.5–1.0 min. Both wild type and mutants received an identical dose of urocortin (0.1 $\mu$g in 200 $\mu$l of 0.9% saline) and saline (as a control).

The doses used were determined from preliminary experiments with reference to data obtained from corresponding studies in Sprague Dawley rats (2). In order to verify that the lack of cardiovascular response to the urocortin injection in mutants was not attributed to the loss of ability of the mice to vasodilate, the mutant mice also received a second infusion of sodium nitroprusside (0.8 $\mu$g in 100 $\mu$l of 0.9% saline) following recovery of arterial pressure from the urocortin infusion. The mean arterial pressure (MAP) was determined from the blood pressure tracings.

Intravenous infusion of urocortin (0.1 $\mu$g) resulted in a prominent depressor response (−28.3±2.0 mm Hg) in control mice (FIG. 6). The reduction in arterial pressure persisted throughout the recording period (90–120 min). In stark contrast, the mutants showed no measurable responses to urocortin[only 1 mutant mouse examined showed a very small and transient reduction (−3.5 mm Hg) in arterial pressure which is likely attributable to the injection pressure itself (FIG. 6)]. In order to verify that the peripheral vasculature of the mutants was able to vasodilate in response to another stimulus, sodium nitroprusside (NP), which causes vasodilation as a nitric oxide donor, was administered to mutant mice. A rapid and robust depressor response was consistently observed in response to the sodium nitroprusside injection (−30.0±5.0 mm Hg) as shown in FIG. 6 (white bar). Basal MAP under anesthesia was not significantly different between the mutant (76 mm Hg) and wild type mice (74 mm Hg) during this experiment.

EXAMPLE 12
CRFR2 Affects Vascularization

Histological analysis of organs from the CRFR2 mutant mice revealed that vascularization of several organs including the brain, the pituitary, and adrenal glands is markedly increased in the CRFR deficient mice (data not shown). This indicates that CRFR2 may act as a direct regulator of vascularization. Ligands serving as agonists or antagonists of CRFR2 can thus be used for manipulation of vascularization in disease states. One example is cancer where increased vascularization is essential for the growth of cancer cells. By stimulating CRFR2 activity, an agonist can be used to inhibit vascularization and thus hinder the growth of cancer cells.

EXAMPLE 13
Summary of Effects of CRFR2 Deletion on Anxiety and Stress

The results presented here suggest that the CRFR2 null mutant mice display a stress-sensitive and anxiety-like phenotype. Although basal feeding and weight gain were normal, mutant mice responded to food deprivation by consuming less food during the refeeding period following the stress of food deprivation. While this may be an effect of metabolism, as the mutant and control animals show no differences in body weight gain or loss during the experiment, it is possible that the stress of food deprivation alters the anxiety state of the animal, thus decreasing their appetite or affecting their metabolism. The mutant mice also displayed a rapid HPA response to restraint stress, again suggesting that these animals are more sensitive to stress. The decrease in ACTH levels in the mutants observed following ten minutes of restraint may be the result of a more rapid negative glucocorticoid feedback on the hypothalamus, since the mutant mice showed higher steroid levels earlier than the control mice. Therefore, the possibility of a second mechanism leading to activation of the adrenal gland in the mutant mice cannot be ruled out. Taken together, the feeding and HPA axis results suggest a hypersensitivity to stress in the CRFR2 mutant mice, although other physiological explanations may be possibly involved in either the altered feeding response or the increased rate in which the HPA axis in the mutant mice responds to stress.

The mutant mice also displayed increased anxiety-like behavior in the EPM and open field tests. However, these mice show similar levels of anxiety-like behavior in the light/dark box. Although pharmacological sensitivity and specificity has generally been demonstrated across many animal tests of anxiety, task differences are sometimes observed (17, 18). Performance in the light/dark paradigm may differ in that this task correlates more with responses to novelty (neophobia) than with exploration (19) while performance in the EPM is determined by exploration of aversive environments (19). Light conditions during testing can also significantly influence the ability to detect anxiolytic or anxiogenic effects in animal tests (17). This profile of results for the CRFR2 mutant mice demonstrates heightened emotionality related to exploration of aversive environments but not neophobia. The results obtained with the CRFR2 mutant mice suggest that these differences in behavioral tests may explain differences in anxiety-like behavior detected in the mice.

EXAMPLE 14
Possible Effects of Increased CRF in cAmyg on Anxiety

Increased CRF mRNA in the cAmyg may explain the anxiety-like behavior and increased HPA axis sensitivity of the mutant mice, since this nucleus expresses CRFR1 (8) and plays a major role in transduction of stress signals (20). In addition, the septum, which contains an abundance of CRFR2, has been shown to modulate the activity of the amygdala (21–23) and lesions of this nucleus result in decreased ACTH secretion following restraint stress (24–27). Lesions of the amygdala have been shown to block CRF-induced anxiety (20) as well as hyperemotionality resulting from septal lesions (21). This neural pathway may explain the decreased anxiety-like behavior seen in the CRFR1 deficient mice (10) as well as the increased anxiety-like behavior in the CRFR2 deficient mice. Therefore, the CRFR2 mutant mouse provides possible evidence for a novel mechanism of receptor modulation in anxiety-like behavior. It is possible that during stress CRFR2 in the lateral septum modulates activity of the amygdala, and in the absence of CRFR2, unimpeded amygdala activity may result in increased anxiety-like behavior.

CRFR2 in the lateral septum may also function as an inhibitor of PVN actions on HPA responses to stress. Since the mutant mice are deficient for CRFR2 in the lateral septum, stress-induced activation of the PVN may occur more rapidly. Further, CRFR2 is the predominant CRF receptor expressed in the PVN in unstressed animals, whereas CRFR1 is found in the PVN only under stress conditions (28, 29). Therefore, in the absence of CRFR2 during stress local effects on PVN activity may be altered.

EXAMPLE 15
Possible Mechanisms for Anxiety Caused by Increased UCN mRNA in the Rostral EW Increased urocortin mRNA in the rostral EW may be a second mechanism leading to increased anxiety-like behavior in the mutant mice, since urocortin has been shown to induce anxiety-like behaviors when injected intravenously (30). Additional explanations for the increased anxiety-like behavior, such as heightened sensitivity of the autonomic nervous system (31–33), cannot yet be ruled out. Previous studies using antisense oligonucleotides have found conflicting results regarding the role of CRFR2 in anxiety and behavior, although these reports did show an anxiolytic-like effect by injection of CRFR1 antisense oligonucleotides (34,35).

EXAMPLE 16
CRFR2 Null Mice and the Sensitivity of the Autonomic Nervous System Additional explanations for the increased anxiety-like behavior, such as heightened sensitivity of the autonoinic nervous system (31–33), cannot yet be ruled out. Previous studies using antisense oligonucleotides have found conflicting results regarding the role of CRFR2 in anxiety and behavior (34, 35). Although these reports show an anxiolytic-like effect by injection of CRFR1 antisense oligonucleotides, neither study reported consistent findings regarding injection of the CRFR2 antisense oligonucleotides. While the technique of antisense oligonucleotide injection offers potential promise, it remains under scrutiny since decreased levels of protein cannot be substituted for complete elimination of the target, as is accomplished in a knock-out animal.

EXAMPLE 17
Effect of UCN on Vasodilation

Absence of CRFR2 in the null mutant mice allowed for confirmation of the effect of urocortin on vasodilation. Mutant mice had no response to intravenous urocortin, while wild type animals showed a dramatic decrease in mean arteriole pressure. Injection of nitroprusside resulted in vasodilation in the mutants, thus confirming that the lack of response to urocortin was not due to a physical inability of the mutant vasculature to dilate, but specifically to the absence of CRFR2. These results support the hypothesis that the effect of urocortin on hypotension (2, 16) occurs via action at CRFR2 in the vascular endothelial cells (5, 8), since the CRFR2 mutant mice showed no response to urocortin. Although the physiological stimulus under which UCN-induced vasodilation would most likely occur is not currently known, the effect of urocortin on CRFR2 in the vasculature may be an interesting target in drug development for hypertension.

Summary

In summary, these results demonstrate that CRFR2 deficient mice exhibit increased anxiety-like behavior and a hypersensitive HPA axis in response to stress. CRFR1 and CRFR2mutant mice provide valuable models of anxiety and depression and may further help delineate the molecular mechanisms underlying these diseases. Study of the CRF signaling pathway and its role in the management of anxiety and depression may provide the necessary clues required for the effective treatment of these diseases.

The following references were cited herein:
1. Vale, W., Spiess, J., Rivier, C. & Rivier, J., *Science* 213, 1394–1397 (1981).
2. Vaughan, J., et al, *Nature* 378, 287–292 (1995).
3. Kishimoto, T., Pearse, R. V., 2nd, Lin, C. R. & Rosenfeld, M. G., *Proc. Natl. Acad. Sci. USA* 92, 1108–1112 (1995).
4. Lovenberg, T. W., et al, *Proc. Natl. Acad. Sci. USA* 92, 836–840 (1995).
5. Perrin, M., et al, *Proc. Natl. Acad. Sci. USA* 92, 2969–2973 (1995).
6. Stenzel, P., et al., *Mol. Endocrinol.* 9, 637–645 (1995).
7. Potter, E., et al., *Proc. Natl. Acad. Sci. USA* 91, 8777–8781 (1994).
8. Chalmers, D. T., Lovenberg, T. W. & De Souza, E. B, *J. Neurosci.* 15, 6340–6350 (1995).
9. Miyata, I., et al., *Biochem. Biophys. Res. Commun.* 256, 692–696 (1999).
10. Smith, G. W., et al, *Neuron* 20, 1093–102 (1998).
11. Timpl, P., et al, *Nat. Genet.* 19, 162–166 (1998).
12. Webster, E. L., et al, *Endocrinology* 137, 5747–50 (1996).
13. Bornstein, S. R., et al, *Endocrinology* 139, 1546–55 (1998).
14. Deak, T., et al, *Endocrinology* 140, 79–86 (1999).
15. Spina, M., et al, *Science* 273, 1561–4 (1996).
16. Schilling, L., Kanzler, C., Schmiedek, P. & Ehrenreich, H., *Br. J. Pharmacol.* 125, 1164–1171 (1998).
17. Hogg, S., *Pharmacol. Biochem. Behav.* 54, 21–30 (1996).
18. Rodgers, R. J, *Behav. Pharmacol.* 8, 477–496 (1997).
19. Belzung, C. & Le Pape, G., *Physiol. Behav.* 56, 623–628 (1994).
20. Liang, K. C., et al, *J. Neurosci.* 12, 2313–2320 (1992).
21. King, F. A. & Meyer, P. M, *Science* 128, 655–656 (1958).
22. Melia, K. R. & Davis, M, *Physiol. Behav.* 49, 603–611 (1991).
23. Lee, Y. & Davis, M, *J. Neurosci.* 17, 6424–6433 (1997).
24. Allen, J. P. & Allen, C. F, *Neuroendocrinology* 19, 115–25 (1975).
25. Beaulieu, S., Di Paolo, T. & Barden, N, *Neuroendocrinology* 44, 247–54 (1986).
26. Beaulieu, S., Di Paolo, T., Cote, J. & Barden, N., *Neuroendocrinology* 45, 37–46 (1987).
27. Marcilhac, A. & Siaud, P, *Exp. Physiol.* 81, 1035–1038 (1996).
28. Imaki, T., et al, *Brain Res. Mol. Brain Res.* 38, 166–170 (1996).
29. Imaki, T., et al, *Endocr. J.* 43, 629–638 (1996).
30. Moreau, J. L., Kilpatrick, G. & Jenck, F, *Neutroreport* 8, 1697–701 (1997).
31. Udelsman, R., et al., *Nature* 319, 147–50 (1986).
32. Andreis, P. G., Neri, G. & Nussdorfer, G. G., *Endocrinology* 128, 1198–200 (1991).
33. Andreis, P. G., Neri, G., Mazzocchi, G., Musajo, F. & Nussdorfer, G. G, *Endocrinology* 131, 69–72 (1992).
34. Heinrichs, S. C., Lapsansky, J., Lovenberg, T. W., De Souza, E. B. & Chalmers, D. T., *Regul. Pept.* 71, 15–21 (1997).

35. Liebsch, G., Landgraf, R., Engelmann, M., Lorscher, P. & Holsboer, F, [In Process Citation] *J. Psychiatr. Res.* 33, 153–163 (1999).
36. Bale, T. L. & Dorsa, D. M, *Endocrinology* 136, 27–32 (1995).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A transgenic mouse whose genome comprises a homozygous disruption of the corticotropin releasing factor receptor 2 (CRFR2) gene, wherein said mouse lacks functional CRFR2 and wherein said mouse exhibits a phenotype of increased anxiety behavior, a hypersensitive hypothalamic-pituitary adrenal (HPA) axis response to stress and a muted cardiovascular response to urocortin administration.

2. The transgenic mouse of claim 1, wherein DNA sequences for exons 10, 11 and 12 of said CRFR2 gene are deleted.

3. The transgenic mouse of claim 2, wherein said deletion comprises a replacement of exons 10, 11 and 12 with a neomycin resistance gene.

4. Progeny mice of the mouse of claim 1, where in the progeny mice have a genome comprising a homozygous disruption of the corticotropin releasing factor receptor 2 (CRFR2) gene, wherein said mouse lacks functional CRFR2 and wherein said mouse exhibits a phenotype of increased anxiety behavior, a hypersensitive HPA axis response to stress and a muted cardiovascular response to urocortin administration.

5. A method of screening a compound for anxiety modulating activity, comprising the steps of:
   a) administering a compound to a transgenic mouse whose genome comprises a homozygous disruption of the corticotropin releasing factor receptor 2 (CRFR2) gene, wherein said mouse lacks functional CRFR2 and wherein said mouse exhibits a phenotype of increased anxiety behavior;
   b) testing the mouse of step a) for anxiety-related behavior; and
   c) comparing the anxiety behavior of the mouse of step b) to a second transgenic mouse whose genome comprises a homozygous disruption of the corticotropin releasing factor receptor 2 (CRFR2) gene, wherein said mouse lacks functional CRFR2 and wherein said mouse exhibits a phenotype of increased anxiety behavior that did not receive said compound, thereby determining the anxiety modulating effect of the compound.

6. The method of claim 5, wherein said mice are tested for anxiety using a test paradigm selected from the group consisting of an elevated plus maze, a light/dark box, and an open field test.

7. A method of screening for compounds which control blood pressure, comprising the steps of:
   a) administering a compound to a transgenic mouse whose genome comprises a homozygous disruption of the corticotropin releasing factor receptor 2 (CRFR2) gene, wherein said mouse lacks functional CRFR2 and wherein said mouse exhibits blood pressure alterations associated with anxiety behavior;
   b) testing the mouse of step a) for alterations in blood pressure; and,
   c) comparing alterations of blood pressure of the mouse of step b) to a second mouse, wherein the second mouse is selected from the group consisting of a transgenic mouse whose genome comprises a homozygous disruption of the corticotropin releasing factor receptor 2 (CRFR2) gene, wherein said mouse lacks functional CRFR2 and wherein said mouse exhibits blood pressure alterations associated with anxiety behavior that did not receive said compound, and a wild-type mouse to which said compound was also administered, thereby determining the blood pressure controlling effect of the compound.

8. A method of screening a compound for effects on the response of the hypothalamic-pituitary-adrenal (HPA) axis to stress, comprising the steps of:
   a) administering the compound to a transgenic mouse whose genome comprises a homozygous disruption of the corticotropin releasing factor receptor 2 (CRFR2) gene, wherein said mouse lacks functional CRFR2 and wherein said mouse exhibits a phenotype of a hypersensitive HPA axis to stress;
   b) placing the mouse of step a) in a stress-inducing situation,
   c) monitoring plasma levels of corticosterone and adrenocorticotropic hormone in the mouse of step b)
   d) comparing said levels to those in a transgenic mouse whose genome comprises a homozygous disruption of the corticotropin releasing factor receptor 2 (CRFR2) gene, wherein said mouse lacks functional CRFR2 and wherein said mouse exhibits a phenotype of a hypersensitive HPA to stress that was not placed in said stress-inducing situation, thereby determining the effect of the compound on the response of the hypothalamic-pituitary-adrenal axis to stress.

9. The method of claim 8, wherein said stress-inducing situation is physical restraint-stress.

10. A method of determining the effects of CRFR2 on a second protein, comprising the steps of:
    a) administering an agonist that affects the second protein to a transgenic mouse whose genome comprises a homozygous disruption of the corticotropin releasing factor receptor 2 (CRFR2) gene, wherein said mouse lacks functional CRFR2 and wherein said mouse exhibits a phenotype of increased anxiety behavior;
    b) performing an assay of the second protein, wherein said assay is selected from the group consisting of assays of protein expression and assays of protein activity; and,
    c) comparing assay results of step b) with those obtained from a wild-type mouse which was administered the same agonist, thereby determining the effects of CRFR2 on a second protein.

11. The method of claim 10, wherein said second protein is selected from the group consisting of corticotropin releasing factor, corticotropin releasing factor receptor 1, urocortin, corticotropin receptors and urocortin receptors.

* * * * *

UNITED STATES PATENT AND TRADEMARK OFFICE
CERTIFICATE OF CORRECTION

PATENT NO.     : 6,353,152 B1
DATED          : March 5, 2002
INVENTOR(S)    : Kuo-Fen Lee, Wyli W. Vale, Tracy L. Bale and George W. Smith It is certified that error appears in the above-identified patent and that said Letters Patent is hereby corrected as shown below:

Column 2,
Line 42, please insert the word -- invention -- between the words "present" and "involves".

Column 4,
Line 33, "present" should read -- presence --.

Column 6,
Line 26, please delete the space in "b e".

Column 8,
Line 21, please insert the word -- to -- between the words "directed" and "the".

Column 9,
Line 16, "week" should read -- weeks --.
Line 40, "Dosta" should read -- Costa --.

Column 10,
Line 13, "pellet" should read -- pellets --.

Column 17,
Line 36, please delete the space in "where in".

Signed and Sealed this

Fifth Day of November, 2002

Attest:

JAMES E. ROGAN
Attesting Officer      Director of the United States Patent and Trademark Office